US012606841B2

(12) United States Patent
Zhang et al.

(10) Patent No.: US 12,606,841 B2
(45) Date of Patent: Apr. 21, 2026

(54) SESAME SEED SHATTERING RESISTANCE TRAIT REGULATION GENE SIHEC3 AND APPLICATION THEREOF

(71) Applicant: HENAN SESAME RESEARCH CENTER, HENAN ACADEMY OF AGRICULTURAL SCIENCES, Zhengzhou (CN)

(72) Inventors: Haiyang Zhang, Zhengzhou (CN); Hongmei Miao, Zhengzhou (CN); Ming Ju, Zhengzhou (CN); Qin Ma, Zhengzhou (CN); Hengchun Cao, Zhengzhou (CN); Zhanyou Zhang, Zhengzhou (CN); Guiting Li, Zhengzhou (CN); Yinghui Duan, Zhengzhou (CN); Cong Mu, Zhengzhou (CN); Qiuzhen Tian, Zhengzhou (CN); Huili Wang, Zhengzhou (CN); Lingling Qin, Zhengzhou (CN); Yingying Huang, Zhengzhou (CN)

(73) Assignee: HENAN SESAME RESEARCH CENTER, HENAN ACADEMY OF AGRICULTURAL SCIENCES, Zhengzhou (CN)

( * ) Notice: Subject to any disclaimer, the term of this patent is extended or adjusted under 35 U.S.C. 154(b) by 0 days.

(21) Appl. No.: 18/978,226

(22) Filed: Dec. 12, 2024

(65) Prior Publication Data

US 2025/0101449 A1       Mar. 27, 2025

Related U.S. Application Data

(63) Continuation of application No. PCT/CN2024/075020, filed on Jan. 31, 2024.

(30) Foreign Application Priority Data

Jul. 10, 2023    (CN) ......................... 202310838584.9

(51) Int. Cl.
C12N 15/82        (2006.01)
C12Q 1/6895       (2018.01)

(52) U.S. Cl.
CPC ....... *C12N 15/8262* (2013.01); *C12Q 1/6895* (2013.01)

(58) Field of Classification Search
None
See application file for complete search history.

(56) References Cited

FOREIGN PATENT DOCUMENTS

| CN | 108586593 A | 9/2018 |
| CN | 117004617 A | 11/2023 |
| WO | 2004113542 A | 12/2004 |

OTHER PUBLICATIONS

Ju et al. "Deletion of a 1,049 bp sequence from the 5' UTR upstream of the SiHEC3 gene induces a seed non-shattering mutation in sesame" 2024 J. Integrative Agriculture 23(8):2589-2604. (Year: 2024).*

(Continued)

*Primary Examiner* — Matthew R Keogh
*Assistant Examiner* — Rebecca Stephens
(74) *Attorney, Agent, or Firm* — Birchwood IP

(57) ABSTRACT

A sesame shattering resistance trait regulation gene Sihec3 and its application are provided. This gene is located on the third chromosome of sesame, is a recessive control gene, and fully explains the phenotypic variation of the shattering resistance trait. Genetic analysis of the shattering trait was conducted with $F_2$ and $F_{2:3}$ populations derived from a hybrid combination between a shattering resistance mutant M7 and normal shattering material. The research indicates that the seed shattering resistance trait in the tested population is a recessive trait controlled by a single gene. Based on the self-constructed sesame genome fine map and efficient gene mapping technology, the key gene Sihec3 and its (Continued)

allele SiHEC3 regulating the sesame shattering trait were cloned and compared. A corresponding gene marker named SSR1 for the sesame shattering resistance trait was dig. This invention provides a technical foundation for breeding new sesame varieties with shattering resistance trait.

2 Claims, 6 Drawing Sheets

Specification includes a Sequence Listing.

(56)            References Cited

OTHER PUBLICATIONS

Chang et al. ("Comparison of the chemical composition of non-shattering and shattering sesame varieties grown in the Huang-Huai region of China" 2024 J. Food Composition & Analysis 130(106194): 8 total pages). (Year: 2024).*

Ju, M. et al. "Deletion of a 1049 bp sequence from the 5' UTR upstream of SiHEC3 gene induces a seed non-shattering mutation in sesame", Journal of Integrative Agriculture, Nov. 14, 2023, Full text.

Zhang, H.Y. et al. "Identification of a SiCL1 gene controlling leaf curling and capsule indehiscence in sesame via cross-population association mapping and genomic variants screening" BMC Plant Biology, vol. 18, Nov. 22, 2018, p. 296, Abstract.

Dash, M. et al. "Assessment of genetic variability for capsule shattering characters in Indian sesame", Electronic Journal of Plant Breeding, vol. 9, No. 2, Jun. 30, 2018, pp. 490-501.

Zheng L, Yao X D, Zhang X M, et al. Progress and Insights in Breeding of Shattering-Resistant Sesame Varieties[J]. Jiangsu Agricultural Sciences, 2022, 50(1): 20-27. doi:10.15889/j.issn.1002-1302.2022.01.004.

* cited by examiner

SESAME SEED SHATTERING RESISTANCE TRAIT REGULATION GENE SIHEC3 AND APPLICATION THEREOF

CROSS-REFERENCE TO RELATED APPLICATIONS

This application is a continuation of International Application No. PCT/CN2024/075020, filed on Jan. 31, 2024, which claims priority to Chinese Patent Application No. 202310838584.9, filed on Jul. 10, 2023, both of which are hereby incorporated by reference in their entireties.

SEQUENCE LISTING

The present application contains a sequence listing which was filed electronically in XML format and is hereby incorporated by reference in its entirety. Besides, the XML copy is created on Mar. 19, 2025, is named "SESAME SEED SHATTERING RESISTANCE TRAIT REGULA-TION GENE SIHEC3 AND APPLICATION THEREOF-Sequence Listing" and is 31,984 bytes in sizes.

TECHNICAL FIELD

The present disclosure relates to the field of sesame molecular genetic breeding technologies, and in particular, to a sesame seed shattering resistance trait regulation gene Sihec3 and an application thereof.

BACKGROUND

Sesame is one of the oldest oilseed crops in the world and an important specific agricultural product with high quality in China. Sesame seeds are enriched with health-beneficial unsaturated fatty acids, including oleic and linoleic acids, as well as antioxidants such as sesamol and sasamlinol. Thus, sesame is earned the name of "the queen of oilseed crops" (Zhang et al., 2019). Currently, sesame is grown in 75 countries around the world, mainly distributed in the tropical and the subtropical regions of Asia, Africa, and Latin America. China is one of the main producing countries of sesame, with an annual cultivation area of 520,000 hectares and a total of approximately 650,000 tons, accounting for 10-25% of the global output (FAO statistics from 2000-2018). Due to its high yield level and high seed quality, China has the prominent advantages in sesame production, processing, and worldwide trade.

However, at present, sesame cultivation and harvesting processes are mainly performed by manual due to the limits on planting scale, variety characteristics, and the availability of specialized machinery. The low level of mechanization significantly hinders the sustainable growth of the global sesame industry. As to sesame varieties, the key challenge for sesame mechanization cultivation is that most varieties are common with capsule dehiscence and seed shattering traits, which directly causes seeds loss as capsules mature and open. When harvesting is not carried out in time, yield losses can exceed 50%. This character of sesame varieties is incompatible with the requirement for harvest mechanization. Consequently, enhancing the shattering resistance in sesame variety is crucial for improving the mechanization of sesame production.

SUMMARY

Based on the obtained mutant material with seed shattering resistance phenotype, sesame reference genome map and gene cloning technology, the present application discloses a gene Sihec3 regulating the seed shattering resistance trait in sesame. This gene supplies a technical foundation for breeding new sesame varieties with high seed shattering resistance trait.

the gene Sihec3, identified on the 3rd chromosome of sesame, is a recessive gene controlling the phenotypic variation associated with the shattering resistance trait.

The technical solution of the present application is list as follows.

The gene Sihec3, identified on the 3rd chromosome of sesame, is a recessive control gene with a 100% explanation for the phenotypic variation associated with the seed shattering resistance trait.

this gene exhibits a deletion with 1049 base pairs in the promoter region ranging from −1 bp~−1012 bp of and from 1-37 bp in the 5' UTR region, compared to its allele SiHEC3, which leads to the alteration of gene function. That is to say, as the 1049 bp sequence in the promoter region and part of 5' UTR region is deleted, the phenotype presents seed shattering resistant.

the genomic DNA (gDNA) of the Sihec3 gene is 3406 bp in length, includes two exons. The sequence of the gDNA is presented in SEQ ID No. 1 with the UTR region consisting of two parts: 1-84 bp and 3217-3406 bp, and the sequence is as follows:

```
GCTTCTGAATTCATCCCTTCAAAGCTAAATCCTCCTCTTTCACCAGCTCAAGG

GTTGTACTTCTTCTCAGAGTACATTTTGATCATGGATTTGAGCCATCACAGGTTC

ACAAACACCACTTGGGAGCCATACAACATTCCCATGGATCAAGGCCATCTGCTCCA

AGATCAAACCCCTTTTGATCATCATCCACACGCACAATGGCCTTACTTTCCTCCAAT

TCACAGCCAAAACGAGCCGTCGGATTCCTCGCCCACGCAACTCCTCCCGTCTCCG

AATTTCGACCAAATGGGCTCTGCAGCCTTCAAAGCGTCAGAAGCCGGAGATCATC

AAGACGACGAGCCCGAAGAGGAGTTGGGAGCCATGAAAGAGATGATGTTCAAGA

TCGCAGCAATGCAACCCGTCGACATCGACCCGGCCACCATCCGCAAGCCCAGGAG

GCGGAACGTCCGGATCAGCGACGACCCGCAGAGCGTCGCGGCCCGCCACCGCCG

TGAGAGGATCAGTGAGAAGATCCGGATCCTCCAGAGACTGGTCCCCGGGGGCACT
```

-continued

```
AAGATGGACACTGCTTCCATGCTGGATGAAGCCATTCGCTATGTTAAGTTCTTGAA

GAGGCAAATCCGCATACTCCAGGCCAACCACCACCAGCCGCCGTGCATAGGGATC

GCCACTCCCACCGGCGCCGCCACCGCTGAAGAATGGGTGGCGGTAACAACCAAG

GCCACCGCCACCGCCACCGCGGCAGCAGGGACGTCGTCTTCGTACTTGTTTGGAG

GGAACAACAATAACGATGGGGCAGGTGATGATATATCAATCCCATATGTTTTAATTT

AACCATAAGTTTTATATATTGGTGATTAGCATTTCACCATATAAATTAGTATATATAATT

AATTTTGATGATCAAACGTTGTATTATCATAAGGTTTGTATTTAAAAATTCAAAAAA

ATCCATGTGATGATAAGAAAAAGGTTTGTTAGGATATTGTTGACTAAGGGGGCATC

GGAATAATCACAAACGGTTAGCCTGAGTTATTTATTGTGTGTATATATAATATATG

CAAGAAGGGCTTTGGCCCTCACAAACTTCTTTTATTGGACTATATTTTCCCTGCCCG

AAATAAAACAGTGATGTAAGAAAACTTTGAATATCATGACTATACTCTCTCTAACAC

ACACGTAAACCTGCGTGTACGTGTGTGTGTTTGCAGGCTTGTGGAAGAAAGTATAG

CAACCTGCAGAGAGCATATATATATGTGTGTGTGTGTGTGTGTGTTTTATCCCTAAAT

ATTATGTGGATTGATGATGAATTTGCTGGTGTCTGATGGACCACAAGAGGCCAAGA

ATGATTGTGTTCTTTTTGCAGTAGCAGACGCCACTTTCACTGCATATACATCATCATC

ATCATCCATCGATCAAACCCTACTCTTGCAAGAAACTTGACGAGATTTTCCTCAAC

AACATTAAATAACACCACACACGTTTCTTCTTCTCCCTGCATTCAGACAACAATGTT

CAACCTTATAGCACATTGTCCTGAAATCTGCATCGTACAAATACGACTTCTATGTATA

CATTTTCCAGTGTATATGTGTTGCAATTGTGTGCATACACATACTCAGGGATGTGGC

GTGTAAAAGGAATATATACATATATAGATAGATAATGTCATTGTGTGTAATAAATTGTT

AAGTGTGTAGGATAATTAAATGTATTTTTCTCCTATAATTTAGGATAAAAATTAAATG

CCAAATGCTACCAAAATATAGGATTAGAATACTACCCTAGCAAGTCAAAAACAAAA

TAACAAAGAACCTAAGTTATGAGACCAAAAATATGTTTAACCCTTCGTATGTATAAT

TAATGTATATGACCAACTAAGTCGTGTTTATTAAACTTGGGATCTTTTCTTCTCTAAA

TTCCTTTTTTTTTTTTTCAAATTTTCTTCTATATATTCATGTGAGGGGGAAATAACAC

TTTTCGTCCATTAATTTAGAGCCTTTTCGTTTTTGGTTCCTTTAATTACAGAATTCTC

ACTAGTGGTTCTGCAACTCCTAAAAAATAGCATTTTTACTCCTATAACACACTTTTG

AGCTGCTAAATTGGTATCCAATGCCTGCATGCATAGTATGATGAATTGTTTGTTAGAT

ACTGAGTGGGAGCACAGCTTTATATGTCTAATTGTATCTTTACTCAGTATTTGTGCA

ATAAAAGTAATACGTAAAATCACACTTATAGGTGTTAATTTGGCTTCTAAACTTATTA

ATTTATAAGATCTTATAACTACATATATTTTATAAAATAATTTAATTATATTTTTAGTCT

CATAATTTTGATCATTCAGCATTTTTAGCTAGTAACTAATCATTTCGGCGGTTTCTGT

TTTCGTGTAACCAGGAGAGATTTGATCGGATTTTTCTCGTGTTTACTAAATTTGTTT

TCAGGTGGGCGGAAAGTGGTATGTGCTACTCAGGTGACTGTTTATAATTAGGGCAA

ATCATCATATTGGCTAATTAATGCCATTTTGATGCCAGAAAGAAAAATTAGCCAATA

GGATGATTCGCCCTAGTTTTCAACAGACACATGAGTGGCAGATACATTTTTCGACC

ATCTCGAAAGAAATCAGGCAAACAGGGGAAAATTGATCAAATTTGTTCTGAATTTG

TTAGAGAAAATATTACATGACAAAATTACAATCTTAACAAGTTAGAGGATTAAATTT

TCAAATGAACATAATTACGGGAGCAAAAATACAATTAAGCCTATAAGATATATATGT

ATATATATAAGATGTTTCTTAAGCTAAGTTGCTAGATTTTATTCTAAAAAGAAGGCTA

TTTAAGTATTTGAATAAAATAAAATTACGAAACTAATTATAATACGTTATTAATAATG
```

-continued

ATAAATTTGTGACTAATTTTTTAAAAAAAATAATATATTTTTAAACTAAGTTGAAAAT

TTTTACTTTTTTCTGAAGAAGCTTATAATTATAAGCTCCAAATCTTAGTTTCCGGATC

GTATAATCTCATTTTCCACAAAATTTACCAAACACTCTGCAACATCTGAAAATTAAG

TTGTATATTACTTTGCCCTATTACAACTACCATTAATTAACGTTTTATGTTCTGATAAT

TAACATATATATATATATACACACACACACATATGTGTGTGTGTTTTTCATAATGCGAT

TTGCAGGTGTGGAAGCATTCAATATGGAGTAAACTTGAAGAGCACATGAACTGCT

GTCGTCGGGGTATTCTCGAGTTCTTCAATATTGTGGGATTCTGACTTGACCCATTGA

GACAAAGTGTGTAGTAGAAACTTCAGTGTATTGGGCTTAATGTTGTAAGAACAGAA

GGGCCCAAAGCCGCCGGAAAAGAGAAGATTGTGTCAGTAGAAAATTACGATCAAG.

A protein encoded by the sesame shattering resistance regulation gene Sihec3 is composed of 244 amino acids, with the corresponding amino acid sequence provided in SEQ ID No. 2:

MDLSHHRFTNTTWEPYNIPMDQGHLLQDQTPFDHHPHAQWPYFPPIHSQN

EPSDSSPTQLLPSPNFDQMGSAAFKASEAGDHQDDEPEEELGAMKEMMFK

IAAMQPVDIDPATIRKPRRRNVRISDDPQSVAARHRRERISEKIRILQRL

VPGGTKMDTASMLDEAIRYVKFLKRQIRILQANHHQPPCIGIATPTGAAT

AEEWVAVTTKATATATAAAGTSSSYLFGGNNNNDGAGVEAFNME;

correspondingly, the cDNA sequence of the sesame seed shattering resistance regulation gene Sihec3, corresponding to the shattering resistance phenotype is 735 bp in length (SEQ ID No. 5). Compared to the cDNA sequence of its allele SiHEC3, there is mutation at 111th nucleotide position where adenine (A) is substituted by cytosine (C). This point mutation leads to an amino acid change at the 37th position of the encoded protein, converting glutamine (Q) to histidine (H). The full cDNA sequence is presented below:

ATGGATTTGAGCCATCACAGGTTCACAAACACCACTTGGGAGCCATACAA

CATTCCCATGGATCAAGGCCATCTGCTCCAAGATCAAACCCCTTTTGATC

-continued

ATCATCCACACGCACAATGGCCTTACTTTCCTCCAATTCACAGCCAAAAC

GAGCCGTCGGATTCCTCGCCCACGCAACTCCTCCCGTCTCCGAATTTCGA

CCAAATGGGCTCTGCAGCCTTCAAAGCGTCAGAAGCCGGAGATCATCAAG

ACGACGAGCCCGAAGAGGAGTTGGGAGCCATGAAAGAGATGATGTTCAAG

ATCGCAGCAATGCAACCCGTCGACATCGACCCGGCCACCATCCGCAAGCC

CAGGAGGCGGAACGTCCGGATCAGCGACGACCCGCAGAGCGTCGCGGCCC

GCCACCGCCGTGAGAGGATCAGTGAGAAGATCCGGATCCTCCAGAGACTG

GTCCCCGGGGGCACTAAGATGGACACTGCTTCCATGCTGGATGAAGCCAT

TCGCTATGTTAAGTTCTTGAAGAGGCAAATCCGCATACTCCAGGCCAACC

ACCACCAGCCGCCGTGCATAGGGATCGCCACTCCCACCGGCGCCGCCACC

GCTGAAGAATGGGTGGCGGTAACAACCAAGGCCACCGCCACCGCCACCGC

GGCAGCAGGGACGTCGTCTTCGTACTTGTTTGGAGGGAACAACAATAAC

GATGGGGCAGGTGTGGAAGCATTCAATATGGAGTAA.

An allele SiHEC3 to gene Sihec3 regulating the sesame seed shattering resistance trait is a complete dominant gene. Sesame varieties containing this allele exhibit the typical seed shattering trait;

the gDNA of the allele SiHEC3 has a sequence length of 3441 bp, and contains two exons. The base sequence is provided in SEQ ID No. 3 as follows (UTR region includes two parts: 1-121 bp and 3264-3441 bp). The complete base sequence is as follows:

AAGCCCTTAAAAGCTGCAGAGAACCTAATCAAAGATTGCTTCTGAATTCATCC

CTTCAAAGCTAAATCCTCCTCTTTCACCAGCTCAAGGGTTGTACTTCTTCTCA

GAGTACATTTTGATCATGGATTTGAGCCATCACAGGTTCACAAACACCACTTGGG

AGCCATACAACATTCCCATGGATCAAGGCCATCTGCTCCAAGATCAAACCCCTTTT

GATCATCATCCACAAGCACAATGGCCTTACTTTCCTCCAATTCACAGCCAAAACGA

GCCGTCGGATTCCTCGCCCACGCAACTCCTCCCGTCTCCGAATTTCGACCAAATGG

GCTCTGCAGCCTTCAAAGCGTCAGAAGCCGGAGATCATCAAGACGACGAGCCCGA

AGAGGAGTTGGGAGCCATGAAAGAGATGATGTTCAAGATCGCAGCAATGCAACCC

GTCGACATCGACCCGGCCACCATCCGCAAGCCCAGGAGGCGGAACGTCCGGATCA

GCGACGACCCGCAGAGCGTCGCGGCCCGCCACCGCCGTGAGAGGATCAGTGAGA

AGATCCGGATCCTCCAGAGACTGGTCCCCGGGGGCACTAAGATGGACACTGCTTC

-continued

CATGCTGGATGAAGCCATTCGCTATGTTAAGTTCTTGAAGAGGCAAATCCGCATAC

TCCAGGCCAACCACCACCAGCCGCCGTGCATAGGGATCGCCACTCCCACCGGCGC

CGCCACCGCTGAAGAATGGGTGGCGGTAACAACCAAGGCCACCGCCACCGCCAC

CGCGGCAGCAGGGACGTCGTCTTCGTACTTGTTTGGAGGGAACAACAATAACGAT

GGGGCAGGTGATGATATATCAATCCCATATGTTTTAATTTAACCATAAGTTTTATATAT

TGGTGATTAGCATTTCACCATATAAATTAGTATATAAATTAATTTTGATGATCAAACG

TTGTATTATCATAAGGTTTGTATTTAAAAATTCAAAAAAATCCATGTGATGATAAGA

AAAAGGTTTGTTAGGATATTGTTGACTAAGGGGGCATCGGAATAATCACAAAACGG

TTAGCCTGAGTTATTTATTGTGTGTATATATAATATATGCAAGAAGGGCTTTGGCC

CTCATAAACTTCTTTTATTGGCCTATATTTTCCCTGCCCGAAATAAAACAGTGATGTA

AGAAAACTTTGAATATCATGACTATACTCTCTCTAACACACACGTAAACCTGCGTGT

ACGTGTGTGTGTTTGCAGGCTTGTGGAAGAAAGTATAGCAACCTGCAGAGAGCAT

ATATATATATATGTGTGTGTGTGTGTGTTTTATCCCTAAATATTATGTGGATTGATG

ATGAATTTGCTGGTGTCTGATGGACCACAAGAGGCCAAGAATGATTGTGTTCTTTT

GCAGTAGCAGACGCCACTTTCACTGCATATACATCATCATCATCCATCGATCAAACC

CTACTCTTGCAAGAAACTTGGCGAGATTTTCCTCAACAACATTAAATAACACCACA

CACGTTTCTTCTTCTCCCTGCATTCAGACAACAATGTTCAACCTTATAGCACATTGT

CCTGAAATCTGCATCGTACAAATACGACTTCTATGTATACATTTTCCAGTGTATATGT

GTTGCAATTGTGTGCATACACATACTCAGGGATGTGGCGTGTAAAAGGAATATATAC

ATATATATATATAATGTCAATGTGTGTAATAAATTGTTAAGTGTGTAGGATAATTAAAT

GTATTTTTTCTCCTATAATTTAGGATAAAAATTAAATACCAAATACTACCAAAATATA

GGATTAGAATACTACCCTAAAAAGTCAAAACAAAAATAACAAATAACCTAAATTAT

GAGACCAAAAATATGTTTAACCCTTCATATGTATGACTTGTATAATTAATGTATTTTA

CCAGCTAAGTCGTGTTTATTAAACTTGGGATCTTTTCTTCTCTATATTCCTTTTTTTTT

TTTTCAAATTTTCTTCTATATATTCATGTGAGGGGGAAATAACACTTTTCGTCCAGTA

ATTTAGAGCCTTTTCATTTTTGGTTCCTTTAGTTACAAAATTCTCATTAGTGGTTCTG

TAACTCCTAAAAAATAGCATTTTTACTCCTATAACACACTTTTGAGCTGCTAAATTG

GTATCCAATGCCTGCATGCATAGTATGATGAATTGTTTGTTAGATACTGAGTGGGAG

CACAGCTTTATATGTCTAATTGTATCTTTACTCAATATTTGTGCAATAAAAGTAATAC

GTAAAATCACACTTATAGGTGTTAATTTGGCTTCTAAACTTATTAATTTATAAGATCT

TATAACTACATATATAAAATAATTTAATTATATTTTTAGTCTCATAATTTTGATCATTCA

GCATTTTTAGCTAGTAACTAATCATTTCGGCGTTTTCTGTTTTCGTGTAACCAAGAG

AGATTTGATCGGATTTTTCTCGTGTTTACTAAATTTGTTTTCAGGTGGGCGAAAAGT

GGTATGTGCTACTCAGGTGACTGTTTATAATTAGGGCAAATCATCATATTGGCTAATT

AATGCCATTTTGATGCCAGAAAGAAAATTAGCCAATAGGATGATTCGTCCTAGTTTT

CAACAGACACATGAGTGGCAGATACATTTTTCGACCATCTCGAAAGAAATCAGGC

AAACAGGAAAAAATTGATCAAATTTGTTCTGAATTTGTTAGAGAAAAAATTACATG

ATCAAATTACAATCTTAACAAGTTAGAGGATTAAATTTTCAAATGGACAAAATTACG

GGAGTAAAAATACAATTAAGCCTATAAGATATATATGTATATATATAAGATGTTTCTTA

AGCTAAGTTGCTAGATTTTATTCTAAAAAGAAGGCTATTTAAGTATTTGAATAAAAT

-continued

```
AAAATTACGAAACTAATTATAATACGTTATTAATAATGATAAATTTGTGACTAATTTT

AAAAAAAATTAATATATTTTTAAACTAAGTTGAAAATTTTTACTTTTTTCTGAAGAA

GCTTATAATTATAAGCTCCAAATCTTAGTTTCCGGATCGTATAATCTCATTTTCCACA

AAATTTACCAAACACTCTGCAACATCTGAAAATTAAGTTGTATATTACTTTGCCCTA

TTACAACTACCATTAATTAACGTTTTATGTTCTGATAATTAACATATATATATACAC

ACACACACACATATGTATGTGTGTTTTTCATAATGCGATTTGCAGGTGTGGAAGCAT

TCAATATGGAGTAAACTTGAAGAGCACATGAACTGCTGTCGTCGGGGTATTCTC

GAGTTCTTCAATATTGTGGGATTCTGACTTGACCCATTGAGACAAAGTGTGTG

GTAGAAACTTCAGTGTATTGGGCTTAATGTTGTAAGAACAGAAGGGCCCAAA

GCCGCCGGAAAAGAGAAGATTGTGTCAGTAGAAAATTACGATCAAG .
```

The amino acid sequence encoded by the allele SiHEC3 contain 244 amino acids with the amino acid sequence as following (SEQ ID No. 4):

```
MDLSHHRFTNTTWEPYNIPMDQGHLLQDQTPFDHHPQAQWPYFPPIHSQN

EPSDSSPTQLLPSPNFDQMGSAAFKASEAGDHQDDEPEEELGAMKEMMFK

IAAMQPVDIDPATIRKPRRRNVRISDDPQSVAARHRRERISEKIRILQRL

VPGGTKMDTASMLDEAIRYVKFLKRQIRILQANHHQPPCIGIATPTGAAT

AEEWVAVTTKATATATAAAGTSSSYLFGGNNNNDGAGVEAFNME;
``` correspondingly, the cDNA corresponding to the allele SiHEC3 has 735 bp with the base sequence detailed as following (SEQ ID No. 6):

```
ATGGATTTGAGCCATCACAGGTTCACAAACACCACTTGGGAGCCATACAA

CATTCCCATGGATCAAGGCCATCTGCTCCAAGATCAAACCCCTTTTGATC

ATCATCCACAAGCACAATGGCCTTACTTTCCTCCAATTCACAGCCAAAAC

GAGCCGTCGGATTCCTCGCCCACGCAACTCCTCCCGTCTCCGAATTTCGA

CCAAATGGGCTCTGCAGCCTTCAAAGCGTCAGAAGCCGGAGATCATCAAG

ACGACGAGCCCGAAGAGGAGTTGGGAGCCATGAAAGAGATGATGTTCAAG

ATCGCAGCAATGCAACCCGTCGACATCGACCCGGCCACCATCCGCAAGCC

CAGGAGGCGGAACGTCCGGATCAGCGACGACCCGCAGAGCGTCGCGGCCC

GCCACCGCCGTGAGAGGATCAGTGAGAAGATCCGGATCCTCCAGAGACTG

GTCCCCGGGGGCACTAAGATGGACACTGCTTCCATGCTGGATGAAGCCAT

TCGCTATGTTAAGTTCTTGAAGAGGCAAATCCGCATACTCCAGGCCAACC

ACCACCAGCCGCCGTGCATAGGGATCGCCACTCCCACCGGCGCCGCCACC

GCTGAAGAATGGGTGGCGGTAACAACCAAGGCCACCGCCACCGCCACCGC

GGCAGCAGGGACGTCGTCTTCGTACTTGTTTGGAGGGAACAACAATAACG

ATGGGGCAGGTGTGGAAGCATTCAATATGGAGTAA .
```

To amplify the promoter and gene sequences of the seed shattering resistance gene Sihec3 and its allele SiHEC3, and to illustrate the difference between the two sequences, two pairs of PCR primers have been designed for amplification based on the reference genome sequence of sesame variety Yuzhi 11. These primers are as follows:

```
Primer1F forward primer (SEQ ID No. 7):
5'-TGACGGTCCGATTTGTAAGGTG-3',

Primer1R reverse primer  (SEQ ID No. 8):
5'-GAAATTCGGAGACGGGAGG-3';

Primer2F forward primer (SEQ ID No. 9):
5'-AGCTAAATCCTCCTCTTTCACCA-3',

Primer2R reverse primer (SEQ ID No. 10):
5'-ACAGCGTACAGGTTTCATT-3';
``` as PCR amplification is conducted using the two primer pairs, genomic DNAs from germplasm resources with shattering trait or shattering resistance trait are used as templates, respectively.

with the Primer1F/R primer set, the amplification for shattering and shattering resistance materials produces 1392 bp and 2432 bp band, respectively.

with the Primer 2F/R primer set, the amplification for shattering and shattering resistance materials produces 3410 bp and 3408 bp band, respectively.

based on amplicon sequencing and sequence alignment with the reference genome, the 1111 bp upstream sequence and 3406 bp gDNA sequence for the sesame shattering resistance gene Sihec3 and the 2114 bp upstream sequence and 3441 bp gDNA sequence of the allele SiHEC3 are obtained;

sequence comparison results show that the most notable difference between the sesame shattering resistance gene Sihec3 and allele SiHEC3 is that Sihec3 lacks 1012 bp promoter sequence and 37 bp gene sequence, compared to the allele SiHEC3, besides of some bases changes in the promoter region.

It should be explained that, as the primer pairs are designed, the amplification product with the first primer pair Primer1F/R contains the promoter and partial gene sequences, while the amplification product with the second primer pair Primer2F/R contains partial gene and gene downstream sequences; and a specific amplification sequence is as follows.

The PCR amplification with two primer pairs for sesame materials with seed shattering resistance are as follows (4543 bp, including the upstream, UTR, CDS, and intron sequences) (SEQ ID No. 13):

TGACGGTCCGATTTGTAAGGTGATAGGGATGATCGAAAGATTGTTTCCCCAACCT

TGGATGCATTAGACGtTGCTGCTGGAAGTGGCGTGCTACGACCATATTAACGTGATA

CAGGAGGCGTACCACTAGACATAATTAATACAAATTATAGTAAACATTAGTTTTTATA

ATTGCTGAAAAAATTAACCTAATTCAATAATTTATGTTGAATTTATGATTATTGTACT

CATTAATTACTTAAAAATATATAGTTCCTTTGTACACATATACAAACGGGTCAAGCAT

TGCTTTTAACTTCTTTAGCATATCACATAAATTTTTTTGTTATAGTACTACTCCAGTTT

GTCCACTCTTTTTCTGTCAACATTGTCTTCTCTTTACAAATAAGAATGGATAAACCT

GACTAATTCATTCTACTAAGAAAAAATCACTTGATGAGCTAAAAAAGCTAAAGCAA

TGCTTGATCCATTTGTACATGGGCACAAAGAAACTATACATTTTTAATGACTCTTATT

GAAAATATTATTATTGGAACTATTAGCCTAATATTGTGATTATTGACATAATTATGTAA

ATAGTGTTATGTGAATACTAGTCTTGTGATTGTTAATATTATTATGTAAATAATGTTAT

TATTGTGAATATTAGTCTAATTTTGCGATTGTTGACATTATTATGTAAATAATGTTATT

ATTTAGAATATTGAATAACGTTGTGATTATTGATATTATTATGTAAATAATATTATTCTT

GAAAATATTAGCCTAAATTTTGTGATTATTGACATTATTTTGTAAATAATATTATTATT

GAGAATATTGATCTAATTTTATGATTATTGACATTATTAAATAAATAATATTATCATTTG

AAATATTAGCTTAAAGGTTGTGAATACTGACATTGTTATGTAAATAATGTTATTATTG

AAAATTGTAATCGAATTTTGTGATTGTTGACATTATTATGTAAATAATAATATTAATGA

AAAAATGCAAGAATTACATCAATTACACCACTATGTAAATTACACAATATGATACAA

TACACACAAAAATTGGGGTCACGATGTCATATACCAAATTTCATTCCTAATGTGTTC

CAATACTCGCTTCTGAATTCATCCCTTCAAAGCTAAATCCTCCTCTTTCACCAGCTC

AAGGGTTGTACTTCTTCTCAGAGTACATTTTGATCATGGATTTGAGCCATCACAGGT

TCACAAACACCACTTGGGAGCCATACAACATTCCCATGGATCAAGGCCATCTGCTC

CAAGATCAAACCCCTTTTGATCATCATCCACACGCACAATGGCCTTACTTTCCTCCA

ATTCACAGCCAAAACGAGCCGTCGGATTCCTCGCCCACGCAACTCCTCCCGTCTCC

GAATTTCGACCAAATGGGCTCTGCAGCCTTCAAAGCGTCAGAAGCCGGAGATCAT

CAAGACGACGAGCCCGAAGAGGAGTTGGGAGCCATGAAAGAGATGATGTTCAAG

ATCGCAGCAATGCAACCCGTCGACATCGACCCGGCCACCATCCGCAAGCCCAGGA

GGCGGAACGTCCGGATCAGCGACGACCCGCAGAGCGTCGCGGCCCGCCACCGCC

GTGAGAGGATCAGTGAGAAGATCCGGATCCTCCAGAGACTGGTCCCCGGGGGCAC

TAAGATGGACACTGCTTCCATGCTGGATGAAGCCATTCGCTATGTTAAGTTCTTGAA

GAGGCAAATCCGCATACTCCAGGCCAACCACCACCAGCCGCCGTGCATAGGGATC

GCCACTCCCACCGGCGCCGCCACCGCTGAAGAATGGGTGGCGGTAACAACCAAG

GCCACCGCCACCGCCACCGCGGCAGCAGGGACGTCGTCTTCGTACTTGTTTGGAG

GGAACAACAATAACGATGGGGCAGGTGATGATATATCAATCCCATATGTTTTAATTT

AACCATAAGTTTTATATATTGGTGATTAGCATTTCACCATATAAATTAGTATATATAATT

AATTTTGATGATCAAACGTTGTATTATCATAAGGTTTGTATTTAAAAATTCAAAAAA

ATCCATGTGATGATAAGAAAAAGGTTTGTTAGGATATTGTTGACTAAGGGGGCATC

GGAATAATCACAAAACGGTTAGCCTGAGTTATTTATTGTGTGTATATATATAATATATG

CAAGAAGGGCTTTGGCCCTCACAAACTTCTTTTATTGGACTATATTTTCCCTGCCCG

AAATAAAACAGTGATGTAAGAAAACTTTGAATATCATGACTATACTCTCTCTAACAC

ACACGTAAACCTGCGTGTACGTGTGTGTGTTTGCAGGCTTGTGGAAGAAAGTATAG

-continued

```
CAACCTGCAGAGAGCATATATATATGTGTGTGTGTGTGTGTGTGTTTTATCCCTAAAT

ATTATGTGGATTGATGATGAATTTGCTGGTGTCTGATGGACCACAAGAGGCCAAGA

ATGATTGTGTTCTTTTTGCAGTAGCAGACGCCACTTTCACTGCATATACATCATCATC

ATCATCCATCGATCAAACCCTACTCTTGCAAGAAACTTGACGAGATTTTCCTCAAC

AACATTAAATAACACCACACACGTTTCTTCTTCTCCCTGCATTCAGACAACAATGTT

CAACCTTATAGCACATTGTCCTGAAATCTGCATCGTACAAATACGACTTCTATGTATA

CATTTTCCAGTGTATATGTGTTGCAATTGTGTGCATACACATACTCAGGGATGTGGC

GTGTAAAAGGAATATATACATATATAGATAGATAATGTCATTGTGTGTAATAAATTGTT

AAGTGTGTAGGATAATTAAATGTATTTTTCTCCTATAATTTAGGATAAAAATTAAATG

CCAAATGCTACCAAAATATAGGATTAGAATACTACCCTAGCAAGTCAAAAACAAAA

TAACAAAGAACCTAAGTTATGAGACCAAAAATATGTTTAACCCTTCGTATGTATAAT

TAATGTATATGACCAACTAAGTCGTGTTTATTAAACTTGGGATCTTTTCTTCTCTAAA

TTCCTTTTTTTTTTTTTCAAATTTTCTTCTATATATTCATGTGAGGGGGAAATAACAC

TTTTCGTCCATTAATTTAGAGCCTTTTCGTTTTTGGTTCCTTTAATTACAGAATTCTC

ACTAGTGGTTCTGCAACTCCTAAAAAATAGCATTTTTACTCCTATAACACACTTTTG

AGCTGCTAAATTGGTATCCAATGCCTGCATGCATAGTATGATGAATTGTTTGTTAGAT

ACTGAGTGGGAGCACAGCTTTATATGTCTAATTGTATCTTTACTCAGTATTTGTGCA

ATAAAAGTAATACGTAAAATCACACTTATAGGTGTTAATTTGGCTTCTAAACTTATTA

ATTTATAAGATCTTATAACTACATATATTTTATAAAATAATTTAATTATATTTTTAGTCT

CATAATTTTGATCATTCAGCATTTTTAGCTAGTAACTAATCATTTCGGCGGTTTCTGT

TTTCGTGTAACCAGGAGAGATTTGATCGGATTTTTCTCGTGTTTACTAAATTTGTTT

TCAGGTGGGCGGAAAGTGGTATGTGCTACTCAGGTGACTGTTTATAATTAGGGCAA

ATCATCATATTGGCTAATTAATGCCATTTTGATGCCAGAAAGAAAAATTAGCCAATA

GGATGATTCGCCCTAGTTTTCAACAGACACATGAGTGGCAGATACATTTTTCGACC

ATCTCGAAAGAAATCAGGCAAACAGGGGAAAATTGATCAAATTTGTTCTGAATTTG

TTAGAGAAAATATTACATGACAAAATTACAATCTTAACAAGTTAGAGGATTAAATTT

TCAAATGAACATAATTACGGGAGCAAAAATACAATTAAGCCTATAAGATATATATGT

ATATATATAAGATGTTTCTTAAGCTAAGTTGCTAGATTTTATTCTAAAAAGAAGGCTA

TTTAAGTATTTGAATAAAATAAAATTACGAAACTAATTATAATACGTTATTAATAATG

ATAAATTTGTGACTAATTTTTTAAAAAAAATAATATATTTTTAAACTAAGTTGAAAAT

TTTTACTTTTTTCTGAAGAAGCTTATAATTATAAGCTCCAAATCTTAGTTTCCGGATC

GTATAATCTCATTTTCCACAAAATTTACCAAACACTCTGCAACATCTGAAAATTAAG

TTGTATATTACTTTGCCCTATTACAACTACCATTAATTAACGTTTTATGTTCTGATAAT

TAACATATATATATATATACACACACACATATGTGTGTGTGTTTTTCATAATGCGAT

TTGCAGGTGTGGAAGCATTCAATATGGAGTAAACTTGAAGAGCACATGAACTGCT

GTCGTCGGGGTATTCTCGAGTTCTTCAATATTGTGGGATTCTGACTTGACCCATTGA

GACAAAGTGTGTAGTAGAAACTTCAGTGTATTGGGCTTAATGTTGTAAGAACAGAA

GGGCCCAAAGCCGCCGGAAAAGAGAAGATTGTGTCAGTAGAAAATTACGATCAAG

TGTGTGAAATGAAACCTGTACGCTGT.
```

The PCR amplification with two primer pairs for sesame materials with seed shattering trait are as follows (5581 bp, including gene upstream, UTR, CDS, and intron sequences) (SEQ ID No. 14):

```
TGACGGTCCGATTTGTAAGGTGATAGGGATGATTGAAAGATTGTTTCCCCAACCT

TGGATGCATTAGACGGTGCTGCTGGAAGTGGCGTGCTACGACCATAGTAACGTGAT

ACAGGAGGCGCACCACTAGACATAATTAATACAAATTATAATAAACATTAGTTTTTA

TAATTGCCGAAAAAATTAACCTAATTCAATAATTTATGTTGAATTTATGATTATTGTA

CTCATTAATTACTTAAAAATATATAGTTCCTTTGTACAGATATACAAACGGGTCAAGC

ATTGCTTTTAACTTCTTTAGCATATCACATAAATTTTTTTGTTATACTACTACTCCAGT

TTGTCCACTCTTTTTCTGTCAACATTGTCTTCTCTTTACAAATAAGAATGGATAAAC

TTGACTAATTAATTCTACTGAGAAAAAATCACTTGATGAGCTAAAAAAGCTAAAGC

AATGCTTGATCCATTTGTACATGGGCACAAAGAAACTATACATTTTTAATAACTCTTA

TTGAAAATATTATTATTGGAACTATCAGCCTAATATTGTGATTATTGACATAATTATGT

AAATAGTATTATGTGAATACTAGTCTTGTGATTGTTAATATTATTATGTAAATAATGTT

ATTATTGTGAATATTAGTCTAACTTTGCGATTGTTGACATTATTATGTAAATAATATTA

TTATTTAGAATATTGAATAATGTTGTGATTATTGATATTATTATGTAAATAATATTATTC

TTGAAAATATTAGCCTAAATTTTGTGATTATGACATTATTTTGTAAATAATATTATTAT

CGGGAATATTGATCTAATTTTATGATTATTGACATTATTAAATAAATAATATTATCATTT

GAAATATTAGCTTAAAGGTTGTGAATACTGACATTGTTATGTAAATAATGTTATTATT

GAAAATTGTAATCGAATTTTATGATTGTTGACATTATTATGTAAATAATAATATTAATG

AAAAAATACATGAATTACACCACTATGTAAATTACACAATATGATACAATACACACA

AAAATTGGGGGTCATGATGTCATATACCAAATTTCATTCCTAATGTGTTCCAATACTC

GTTTCAATGTGAAACGGTCGAGTTATCCGTGTCAAATTCTATTTTTTCTTTTTTTGTA

GTGTATGACTATTACAGCTCTGAGCATGTCTCAAATAATAATTATCTTTGTTTTTGAA

CAAAAATATTAATTATCTTTAATGCATAGAGAAATGGCTATTTTTAAGCTGTAAAGA

AGCAATTATATGAGAGTGAGAGCTCTTAGTTTAGACAATTATTGATAACTCATCAGC

AAGTGCATTTGATTGTGAGGTCATTATCACCATTAATAAAAGTGATCATAACATCAA

TATCATCAGTAATCATGTTTATGATCAATTAATCAGAATAATTCAATTCGTCTTTGCT

GTGTAATTTGATTTTTTACAATAAAACTTAATTGCATTTTTAGTTCAAAAATTATATA

CAATTATTTGACACTTTAGTCCTGTAATTTATTTGAGTTATAAAAGTAGTCTCATTTT

TTTTAATTCTGCAATTTTAAGACAAAATTGGTCAAATATTCAAAGTTGACCTGAATT

CTGATGCCACTTTTCAGCTAATTTTAAAAATTTCAATCAGATTTGCCATAAACTTGC

AAAATTAAAATAAGGTGAAGAACTAATTTACAACCTAATTAACAAGTTACCAAACT

AATATAAAAATGACTATAATTTTGTTTAAATCTAATAATTATGAAATGAATAATAGCTT

TTCTCATTGAATATTTTATTCATAATATATGATTCTTTTTTTGTGTTCAATAAAGAATAT

GGGGAACCGTACTTGGGATGGAAAGCCTTGTTTGAAAACAGCAAACCCTAGAAAG

GGTTCTAACAATCTGCAATGAAAAAATTCACAGCCCTTTACTTCATCATTTCATAGT

ATATCAAAAGGGGTGGTCCCATCAACATTAATCAATCTCCCTACGTTGTTTCTTTCT

CTTTAAATTCCCTCAAATTTCCTCTCTCTCTCTCTCTCTCTCTCTCTCTATATATATATA

TATATATATATATACATACACTTAAATGCATCAAAGCCCTTAAAAGCTGCAGAGAACC

TAATCAAAGATTGCTTCTGAATTCATCCCTTCAAAGCTAAATCCTCCTCTTTCACCA
```

-continued

```
GCTCAAGGGTTGTACTTCTTCTCAGAGTACATTTTGATCATGGATTTGAGCCATCAC

AGGTTCACAAACACCACTTGGGAGCCATACAACATTCCCATGGATCAAGGCCATCT

GCTCCAAGATCAAACCCCTTTTGATCATCATCCACAAGCACAATGGCCTTACTTTCC

TCCAATTCACAGCCAAAACGAGCCGTCGGATTCCTCGCCCACGCAACTCCTCCCGT

CTCCGAATTTCGACCAAATGGGCTCTGCAGCCTTCAAAGCGTCAGAAGCCGGAGA

TCATCAAGACGACGAGCCCGAAGAGGAGTTGGGAGCCATGAAAGAGATGATGTTC

AAGATCGCAGCAATGCAACCCGTCGACATCGACCCGGCCACCATCCGCAAGCCCA

GGAGGCGGAACGTCCGGATCAGCGACGACCCGCAGAGCGTCGCGGCCCGCCACC

GCCGTGAGAGGATCAGTGAGAAGATCCGGATCCTCCAGAGACTGGTCCCCGGGGG

CACTAAGATGGACACTGCTTCCATGCTGGATGAAGCCATTCGCTATGTTAAGTTCTT

GAAGAGGCAAATCCGCATACTCCAGGCCAACCACCACCAGCCGCCGTGCATAGGG

ATCGCCACTCCCACCGGCGCCGCCACCGCTGAAGAATGGGTGGCGGTAACAACCA

AGGCCACCGCCACCGCCACCGCGGCAGCAGGGACGTCGTCTTCGTACTTGTTTGG

AGGGAACAACAATAACGATGGGGCAGGTGATGATATATCAATCCCATATGTTTTAAT

TTAACCATAAGTTTTATATATTGGTGATTAGCATTTCACCATATAAATTAGTATATAAA

TTAATTTTGATGATCAAACGTTGTATTATCATAAGGTTTGTATTTAAAAATTCAAAAA

AATCCATGTGATGATAAGAAAAAGGTTTGTTAGGATATTGTTGACTAAGGGGGCAT

CGGAATAATCACAAAACGGTTAGCCTGAGTTATTTATTGTGTGTATATATATAATATAT

GCAAGAAGGGCTTTGGCCCTCATAAACTTCTTTTATTGGCCTATATTTTCCCTGCCC

GAAATAAAACAGTGATGTAAGAAAACTTTGAATATCATGACTATACTCTCTCTAACA

CACACGTAAACCTGCGTGTACGTGTGTGTGTTTGCAGGCTTGTGGAAGAAAGTATA

GCAACCTGCAGAGAGCATATATATATATATGTGTGTGTGTGTGTGTGTTTTATCCCTA

AATATTATGTGGATTGATGATGAATTTGCTGGTGTCTGATGGACCACAAGAGGCCA

AGAATGATTGTGTTCTTTTGCAGTAGCAGACGCCACTTTCACTGCATATACATCATC

ATCATCCATCGATCAAACCCTACTCTTGCAAGAAACTTGGCGAGATTTTCCTCAAC

AACATTAAATAACACCACACGTTTCTTCTTCTCCCTGCATTCAGACAACAATGTT

CAACCTTATAGCACATTGTCCTGAAATCTGCATCGTACAAATACGACTTCTATGTATA

CATTTTCCAGTGTATATGTGTTGCAATTGTGTGCATACACATACTCAGGGATGTGGC

GTGTAAAAGGAATATATACATATATATATATAATGTCAATGTGTGTAATAAATTGTTAA

GTGTGTAGGATAATTAAATGTATTTTTTCTCCTATAATTTAGGATAAAAATTAAATAC

CAAATACTACCAAAATATAGGATTAGAATACTACCCTAAAAAGTCAAAACAAATATA

ACAAATAACCTAAATTATGAGACCAAAAATATGTTTAACCCTTCATATGTATGACTT

GTATAATTAATGTATTTTACCAGCTAAGTCGTGTTTATTAAACTTGGGATCTTTTCTT

CTCTATATTCCTTTTTTTTTTTTTCAAATTTTCTTCTATATATTCATGTGAGGGGGAAA

TAACACTTTTCGTCCAGTAATTTAGAGCCTTTTCATTTTTGGTTCCTTTAGTTACAAA

ATTCTCATTAGTGGTTCTGTAACTCCTAAAAAATAGCATTTTTACTCCTATAACACAC

TTTTGAGCTGCTAAATTGGTATCCAATGCCTGCATGCATAGTATGATGAATTGTTTGT

TAGATACTGAGTGGGAGCACAGCTTTATATGTCTAATTGTATCTTTACTCAATATTTG

TGCAATAAAAGTAATACGTAAAATCACACTTATAGGTGTTAATTTGGCTTCTAAACT

TATTAATTTATAAGATCTTATAACTACATATATAAAATAATTTAATTATATTTTTAGTCT
```

-continued

```
CATAATTTTGATCATTCAGCATTTTTAGCTAGTAACTAATCATTTCGGCGTTTTCTGT

TTTCGTGTAACCAAGAGAGATTTGATCGGATTTTTCTCGTGTTTACTAAATTTGTTT

TCAGGTGGGCGAAAAGTGGTATGTGCTACTCAGGTGACTGTTTATAATTAGGGCAA

ATCATCATATTGGCTAATTAATGCCATTTTGATGCCAGAAAGAAAATTAGCCAATAG

GATGATTCGTCCTAGTTTTCAACAGACACATGAGTGGCAGATACATTTTTCGACCAT

CTCGAAAGAAATCAGGCAAACAGGAAAAAATTGATCAAATTTGTTCTGAATTTGTT

AGAGAAAAAATTACATGATCAAATTACAATCTTAACAAGTTAGAGGATTAAATTTTC

AAATGGACAAAATTACGGGAGTAAAAATACAATTAAGCCTATAAGATATATATGTAT

ATATATAAGATGTTTCTTAAGCTAAGTTGCTAGATTTTATTCTAAAAAGAAGGCTATT

TAAGTATTTGAATAAAATAAAATTACGAAACTAATTATAATACGTTATTAATAATGAT

AAATTTGTGACTAATTTTAAAAAAAATTAATATATTTTTAAACTAAGTTGAAAATTTT

TACTTTTTTCTGAAGAAGCTTATAATTATAAGCTCCAAATCTTAGTTTCCGGATCGTA

TAATCTCATTTTCCACAAAATTTACCAAACACTCTGCAACATCTGAAAATTAAGTTG

TATATTACTTTGCCCTATTACAACTACCATTAATTAACGTTTTATGTTCTGATAATTAA

CATATATATATATACACACACACACACATATGTATGTGTGTTTTTCATAATGCGATTTG

CAGGTGTGGAAGCATTCAATATGGAGTAAACTTGAAGAGCACATGAACTGCTGTC

GTCGGGGTATTCTCGAGTTCTTCAATATTGTGGGATTCTGACTTGACCCATTGAGAC

AAAGTGTGTGGTAGAAACTTCAGTGTATTGGGCTTAATGTTGTAAGAACAGAAGG

GCCCAAAGCCGCCGGAAAAGAGAAGATTGTGTCAGTAGAAAATTACGATCAAGTG

TGTGAAATGAAACCTGTACGCTGT.
```

A primer pair for PCR to identify the sesame shattering resistance trait gene Sihec3 and its allele SiHEC3 is named SSR1. Considering the target genetic marker sites belong to SV (Structure Variation) mutation, this primer pair are designed as follows:

```
SSR1-F sequence (SEQ ID No. 11):
5'-TACATGGGCACAAAGAAAC-3',

SSR1-R sequence (SEQ ID No. 12):
5'-CTGGTGAAAGAGGAGGATT-3';
``` the PCR amplification products for homozygous sesame shattering resistance or shattering type genomic DNA as template are 1724 bp or 684 bp.

In sesame molecular breeding, the primer pair SSR1 is utilized to detect and determine whether a sesame material exhibit the shattering resistance phenotype or not.

A method for distinguishing the sesame shattering resistance gene Sihec3 and its allele SiHEC3 with the primer pair is composed of the following steps:

(1) extracting genomic DNA from a sesame sample;

(2) With the genomic DNA extracted in step (1) as a template, performing a PCR amplification with the primer pair SSR1 and conducting an agarose gel electrophoresis;

(3) determining the phenotype of sesame sample belongs to shattering or shattering resistance based on electrophoretic band type. The criterion is as follows:

if the amplicon is 1724 bp, the tested sample contains SiHEC3, the gene promoter and 5' UTR sequences are complete, and should be homozygous with shattering phenotype;

if amplicon is 684 bp, the tested sample contains Sihec3, the gene promoter and 5' UTR sequences are incomplete, and should be homozygous with shattering resistance phenotype;

if there are two amplicons with 1724 bp and 684 bp in length, the tested sample should be heterozygous with shattering phenotype.

In order to accelerate breeding new sesame varieties suitable for mechanized production, Henna Sesame Research Center, Henan Academy of Agricultural Sciences systematically carried out sesame physical and chemical mutagenesis, interspecific hybridization, T-DNA transformation and other germplasm creation technology research since 2008. A seed shattering resistance mutant M7 was preliminary obtained and purified from the constructed sesame mutant library.

In order to further determine the key gene regulating sesame shattering trait, the applicant performed the genetic analysis of seed shattering trait using the mutant M7 and the $F_2$ and $F_{2:3}$ population derived from the crosses "M7 (shattering resistance)× Yuzhi Dw609 (shattering)" and "M7 (shattering resistance)× Xiangcheng Dazibai (shattering)". Results have shown that the seed shattering resistance trait in tested population is recessive and controlled by a single gene. Based on self-constructed sesame genome fine map and high-efficient gene mapping techniques, the applicant cloned the target gene Sihec3 and its allele SiHEC3 which regulate the sesame shattering trait and developed the genetic marker for sesame shattering resistance trait.

Overall, the primary techniques and advantages of the present application are as follows: (1) the gene Sihec3 and allele gene controlling sesame seed shattering resistance have been cloned for the first time. Research results indicate that a 1049 bp SV mutation in the promoter and 5' UTR region of this gene causes the change of seed shattering resistance trait. Cloning of this gene supplies the key information for further exploring the sesame seed development and regulation mechanism; (2) the development of the shattering resistance gene marker SSR1 establishes the basis for identifying shattering resistance trait in sesame germplasm resources and provides the crucial technological support for rapid and precise determination of the seed shattering phenotype and seed purity, as well as for new sesame variety breeding with seed shattering resistance; (3) the shattering resistance gene and its gene marker provided in the application offer vital technical guidance for accelerating molecular-assisted breeding process and breeding new varieties and enhancing mechanization level in sesame production.

In conclusion, the present application provides the significant theoretical foundation for research in seed shattering resistance regulation and seed development mechanism in sesame and other crops. This achievement also supplies valuable genetic resources for sesame molecular-assisted breeding technology system construction and more new shattering resistance varieties breeding. The application has the important scientific and economic applied potential.

a: capsules and seeds of the sesame mutant M7 with seed shattering resistance trait; b: capsules and seeds of the sesame germplasm (Yuzhi 11) with seed shattering trait.

Figure 2:
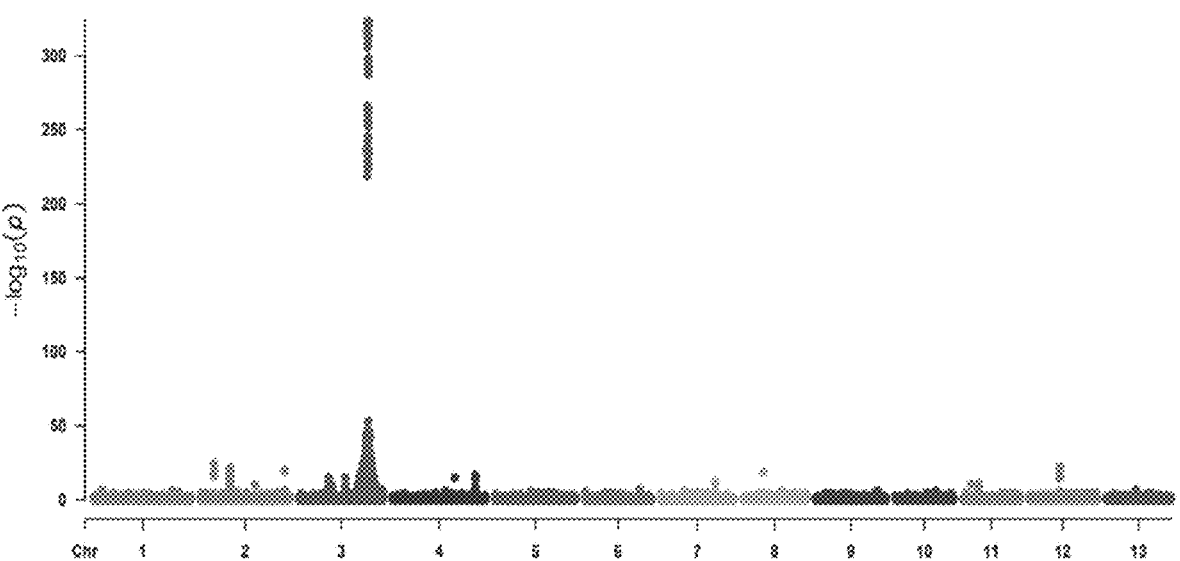

FIG. 2 shows a genome-wide association analysis result of the shattering resistance trait in the hybrid population "M7×Xiangcheng Dazibai" according to the present application.

Figure 3:
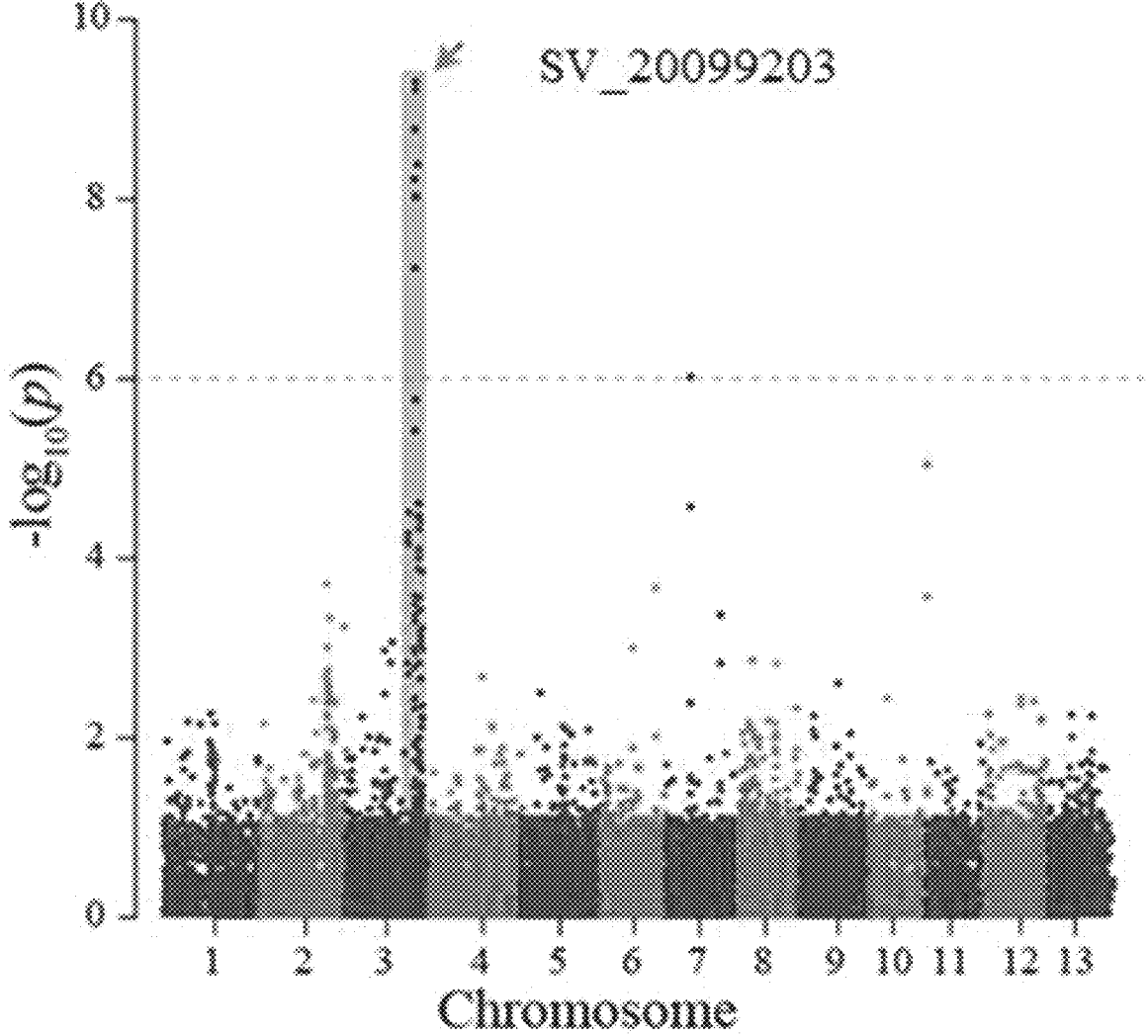

FIG. 3 shows an SV correlation analysis result of the shattering trait in the hybrid population "M7×Xiangcheng Dazibai".

Figure 4:
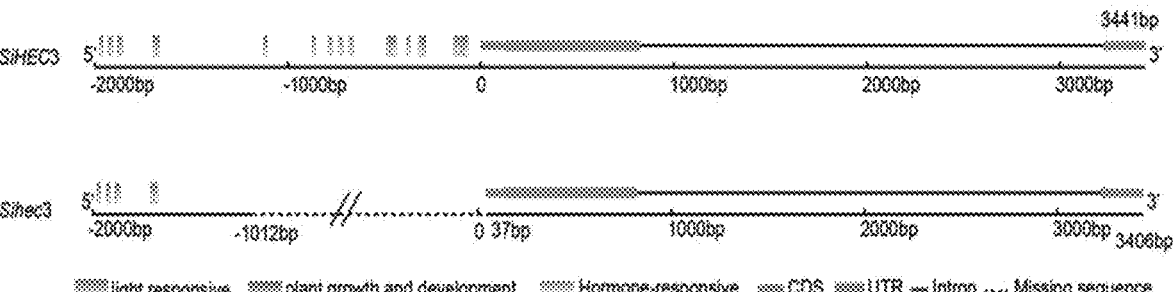

FIG. 4 shows a comparation between a shattering resistance trait gene Sihec3, and its allele gene SiHEC3, as well as their promoter sequences according to the present application.

Figure 5:
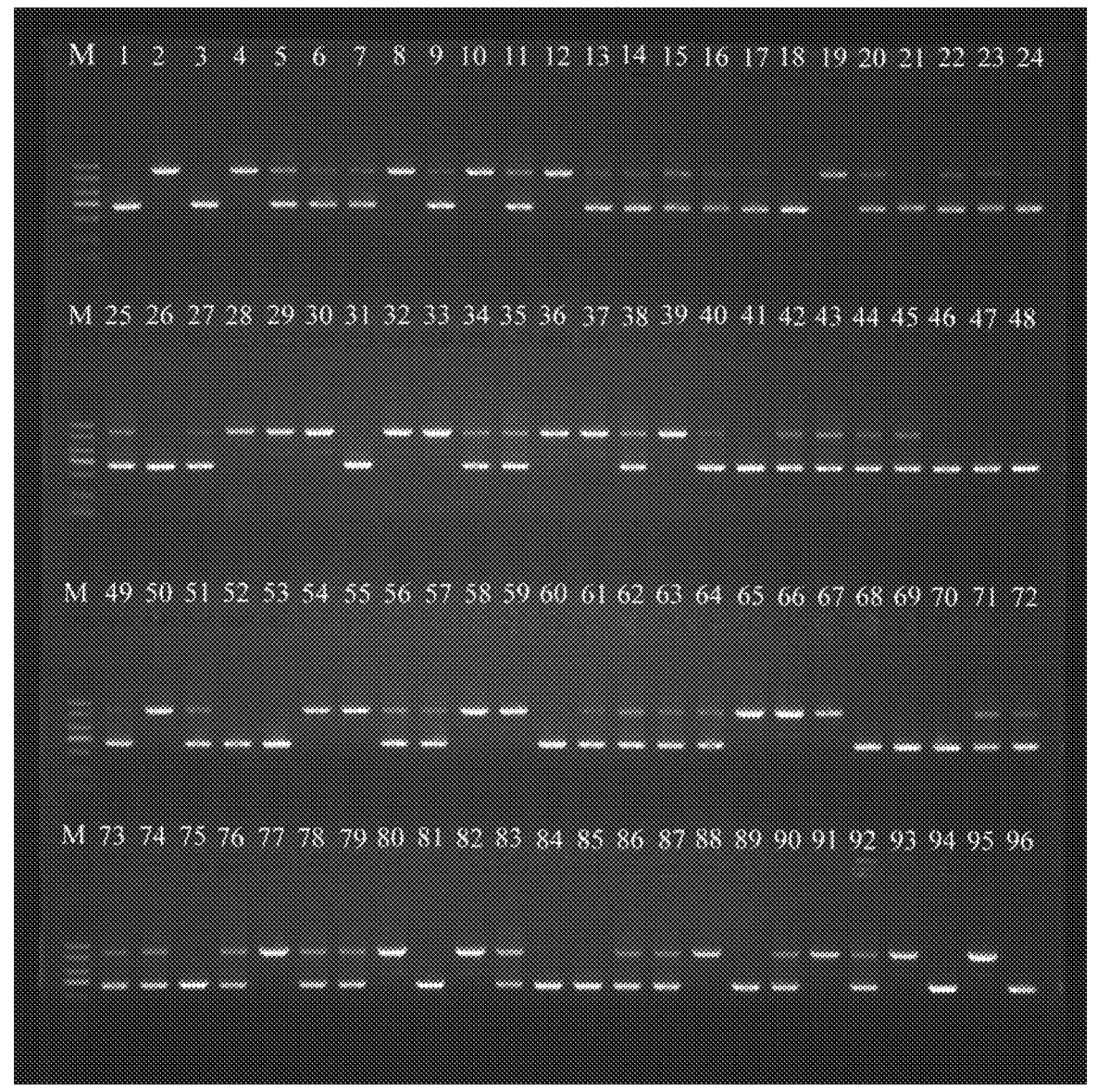

FIG. 5 shows an amplification result of SSR1 marker of partial plantlets in the test $F_2$ population of "Yuzhi NS610× Anhui Qingyangbai" according to the present application;

M: DL2000 (bands from top to bottom are 2000 bp, 1500 bp, 1000 bp, 750 bp, 500 bp, 250 bp, 100 bp in sequence, respectively); lane 1: shattering resistance parents; 2: shattering parents; lane 3-96: some plantlets of test $F_2$ population. 43 plants are heterozygous with shattering trait (containing bands of 1724 bp and 684 bp); 28 plants are homozygous with shattering trait (containing a band of 1724 bp); 22 plants are homozygous with shattering resistance trait (containing a band of 684 bp).

Figure 6:
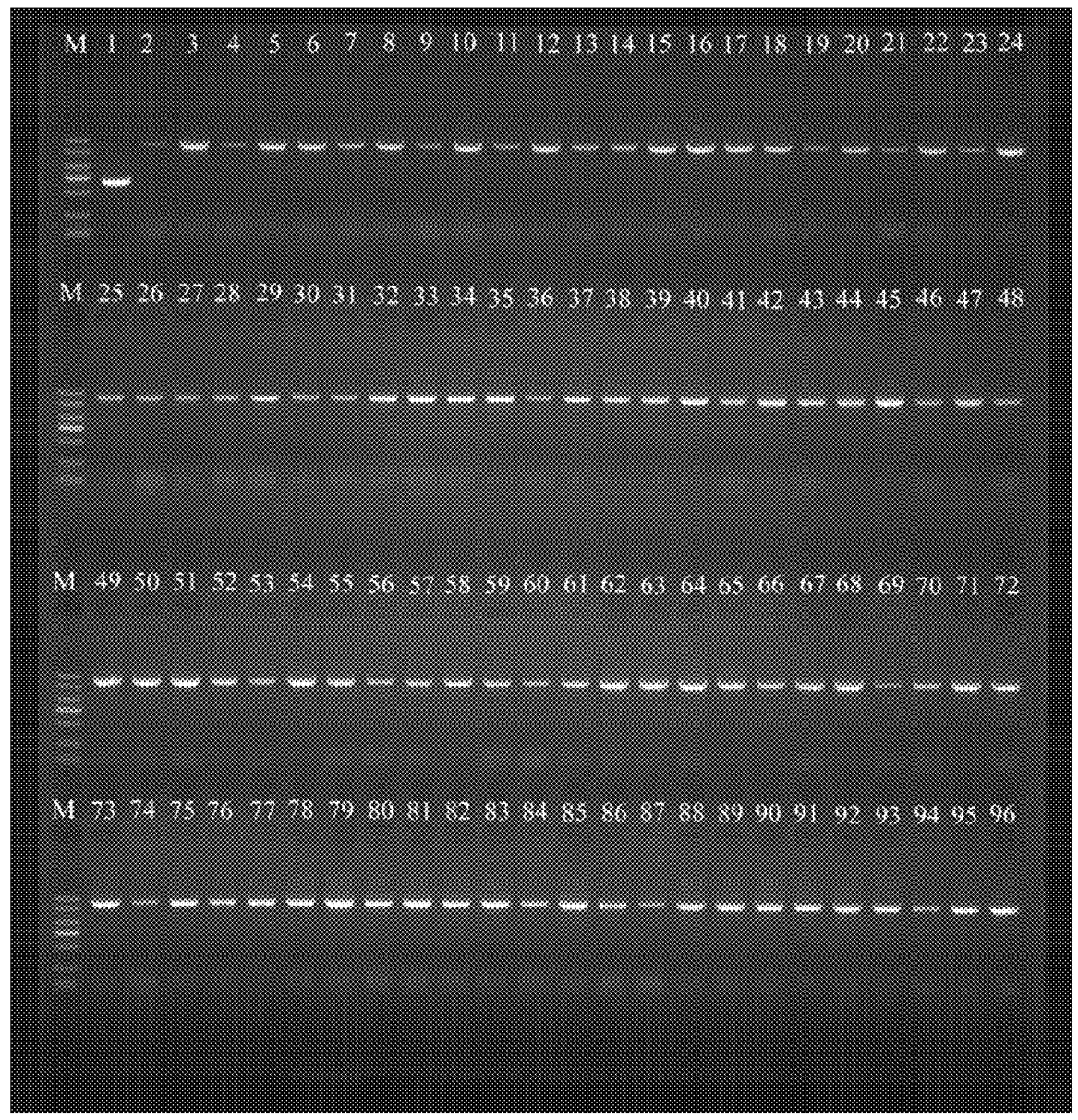

FIG. 6 shows the amplification result of SSR1 marker with 96 sesame germplasm accessions according to the present application;

M: DL2000 (bands from top to bottom are 2000 bp, 1500 bp, 1000 bp, 750 bp, 500 bp, 250 bp, 100 bp in sequence, respectively); lane 1: shattering resistance parents; 2: shattering parents; lane 3-96:96 sesame shattering germplasm accessions (containing a band of 1724 bp).

DESCRIPTION OF EMBODIMENTS

Below is a detailed explanation of the present application, supplemented by the Examples. Before introducing the specific Examples, a brief introduction and explanation of some experimental backgrounds in the following Examples are provided below.

Sesame Materials:

Yuzhi 11, Xiangcheng Dazibai, Anhui Qingyang Bai and other sesame varieties are the main varieties cultivated in sesame production. All these varieties belong to seed shattering materials. M7 is a sesame mutant with seed shattering resistance which was created by Henan Sesame Research Center, Henan Academy of Agricultural Sciences. This line has been effectively utilized for breeding the new sesame variety Yuzhi NS610 which presents the desirable seed shattering resistance trait. All the mentioned germplasm materials are publicly accessible and can be obtained from relevant germplasm resource banks; as a professional research organization, the applicant reserve the relevant sesame germplasm materials for long time.

Example 1

In order to accurately determine the target gene regulating the shattering resistance trait in sesame and to establish the basis for new variety breeding, a further detailed genetic analysis research on this trait has been conducted. Here is a concise overview of the research process.

(I) Genetic background analysis of sesame seed shattering trait

Figure 1:
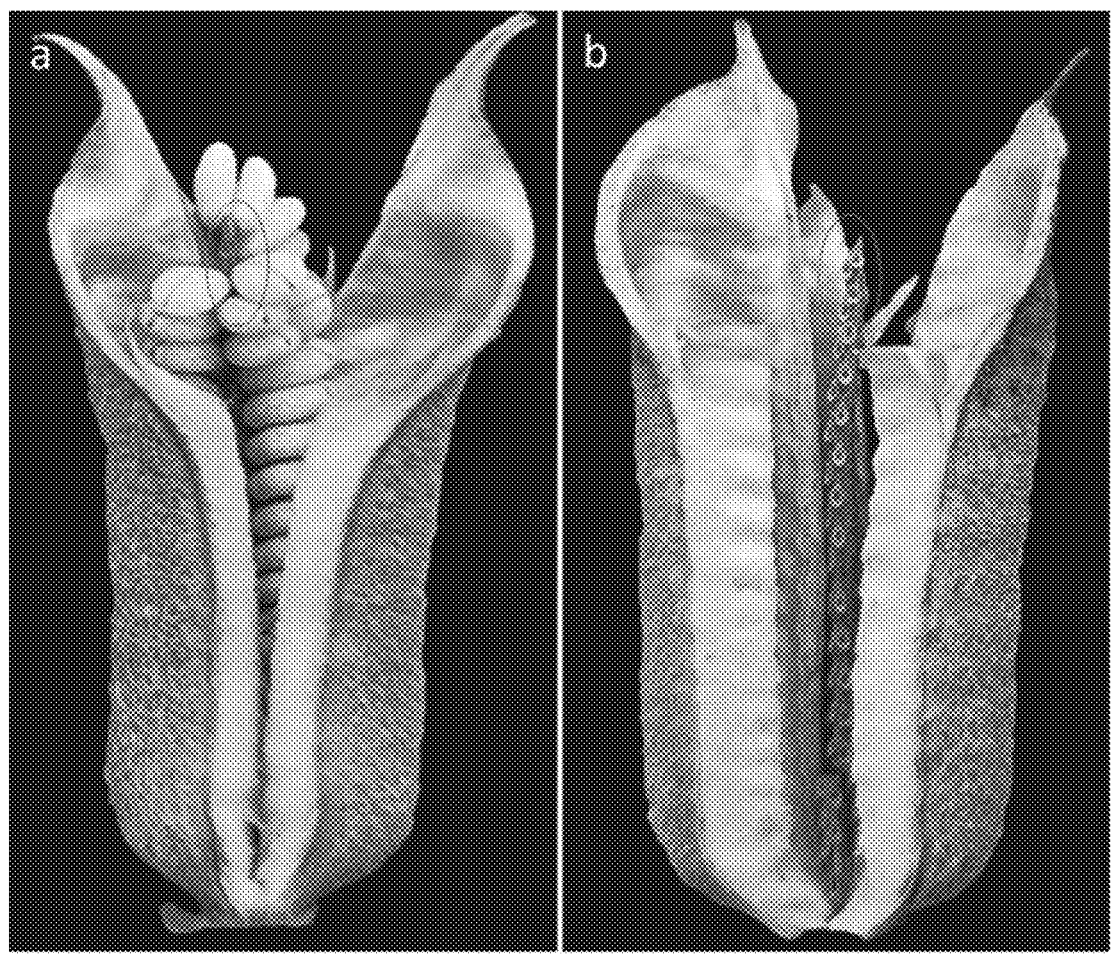
FIG. 1 shows a comparison of capsules and seeds between the mutant with seed shattering resistance trait and a sesame material with seed shattering trait.

During the research, shattering resistance germplasm M7 (shattering resistance) and Xiangcheng Dazibai (shattering) were chosen to construct a hybrid cross (the details of which are presented in Table 1, with the phenotypic comparison illustrated in FIG. 1). The $F_1$ and $F_2$ progeny were evaluated for their phenotypes and statistics analyses.

TABLE 1

Trait analysis of hybrid population from the cross between shattering resistance mutant × shattering genotype material

| Materials | Total number (plant) | Shattering (plant):shattering resistance (plant) | Shattering (plant):shattering resistance (plant) | $\chi^2$ |
|---|---|---|---|---|
| Xiangcheng Dazibai (shattering) ($P_1$) | 15 | 15:0 | — | — |
| M7 (shattering resistance) ($P_2$) | 8 | 0:8 | — | — |
| $F_1$ of reciprocal cross | 18 | 18:0 | — | — |
| $F_1$ of cross combination | 18 | 18:0 | — | — |
| $F_2$ of reciprocal cross | 266 | 209:57 | 3.67:1 | 1.809 |
| $F_2$ of cross combination | 260 | 201:59 | 3.41:1 | 0.739 |

Note:
$\chi^2(0.05, 1) = 3.84$.

The Chi-square test results presented in Table 1 reveal that the ratio of the shattering-to-shattering resistance in the $F_2$ generation of crosses and reciprocal crosses between the shattering resistance mutant and shattering genotype material is approximately 3.67:1 and 3.41:1, respectively. The ratios are consistent with the expected value of 3:1 Mendelian ratio (where $\chi^2$ is less than 3.84). These results suggest that the shattering resistance trait in the hybrid population of mutant M7×Xiangcheng Dazibai accords with the Mendelian inheritance pattern, is a recessive trait, and controlled by a single gene.

(II) Gene Sequencing

During constructing the aforementioned hybrid population, samples of young leaves were collected from individual $F_2$ plantlets for subsequent gene sequencing analysis. Additionally, phenotype investigation and statistical analysis of the $F_{2:3}$ progeny were carried out to determine the homozygous or heterozygous genotype of each $F_2$ plantlet.

According to the phenotype investigation results, 29 $F_2$ plantlets with homozygous shattering trait and 35 $F_2$ plantlets with homozygous shattering resistance were randomly chosen from the tested population. DNA was extracted from leaves of each sample using the improved CTAB method proposed by Wei Libin et al. ("Sesame DNA and RNA synchronous extraction method", Molecular Plant Breeding, 2008), At the same time, DNA of two parents was also extracted individually.

Finally, genome resequencing of the above 64 materials was performed using Illumina sequencing method, with the sequencing coverage of ≥30×.

(III) Genome Wide Association Analysis of the Hybrid Population with Seed Shattering Trait Initially, genome re-sequencing data of each sample was aligned and assembled using the BWA (Burrows-Wheeler Aligner) software, based on the genome data of Yuzhi 11 as the reference genome (reported by Zhang et al. in "Ultra-dense SNP genetic map construction and identification of SiDt gene controlling the determinate growth habit in *Sesamum indicum* L", Science Reports, 2016 and Zhao et al. in "Identification of *sesamum* (*Sesamum indicum* L.) chromosomes using the BAC-FISH system", Plant Biology, 2018).

Further, all the candidate SNPs and Indels within this identified region were screened based on the research basis. After filtered, 83 variants remained within the region. Analysis indicates that these 83 variant sites do not cause gene function variation.

(V) SV Genome Wide Association Analysis of the Hybrid Population with Shattering Resistance Trait To further determine the target gene, a genome-wide association analysis of SVs in two parents and 64 $F_2$ plantlets was performed using LUMPY, Manta, and GRIDSS2 software. To enhance the accuracy of SV detection, the results from different software were cross-validated, filtered, and statistically analyzed.

The results indicate that a total of 31,884 SVs, including 2,786 deletions (DEL), 21 insertions (INS), 5729 inversions (INV), 550 duplications (DUP), and 22,798 translocations (TRA) existed in two parents. The length of these SVs ranged from 30 bp to 23 Mb.

Subsequently, a GLM association analysis was conducted with the population phenotype and SV matrix information.

Based on the target region determined by SNP/Indel association and SV matrix information from the hybrid $F_2$ population, the candidate regions with SV variants were filtered. Elementary results indicated that there are 21 specific SVs within the associated region in the 3rd chromosome of samples with seed shattering resistance trait, as shown in FIG. 3.

Based on the previous work, including the SV matrix library, these 21 SVs were further filtered and screened. The results revealed that the retained 11 SVs were uniquely present in the $F_2$ samples with shattering resistance trait as detailed in Table 2 below.

TABLE 2

Details of 11 candidate SVs in the shattering resistance $F_2$ individual plant

| Chromosome | Location | SV type | Length of SV (bp) | Explanation ratio of variation for shattering resistance trait | Function annotation |
|---|---|---|---|---|---|
| chrom 3 | 19732809 | INV | 454 | 37.14% | Sindi-0761000-upstream-gene-variant |
| chrom 3 | 19857079 | INV | 44 | 62.86% | / |
| chrom 3 | 19903551 | DEL | 164 | 42.86% | Sindi-0763200-downstream-gene-variant |
| chrom 3 | 19903551 | INV | 160 | 28.57% | / |
| chrom 3 | 19915101 | INV | 46 | 2.86% | / |
| chrom 3 | 19918229 | INV | 36 | 2.86% | / |
| chrom 3 | 19921739 | INV | 147 | 5.71% | / |
| chrom 3 | 19983870 | DEL | 348 | 37.14% | Sindi-0763800-upstream-gene-variant |
| chrom 3 | 20099203 | DEL | 1050 | 88.57% | Sindi-0765000-upstream-gene-variant |
| chrom 3 | 20120488 | DEL | 2313 | 88.57% | Sindi-0765200-downstream-gene-variant |
| chrom 3 | 20132827 | DEL | 50 | 5.71% | Sindi-0765400-downstream-gene-variant |

Note:
"/" locus refers to an intergenic region.

Subsequently, reliable SNPs and InDels were detected and filtered using the Genome Analysis Toolkit (GATK).

A total of 1,620,769 variants including SNPs and InDels between the two parents. Combined with the genome resequencing analysis results of the 64 $F_2$ plantlets, a generalized linear model (GLM) association analysis was conducted using Tassele 5.0 software.

As showed in FIG. 2, the final results revealed that the variants closely associated with the shattering resistance trait (with P value less than E-250) were localized on the 3rd chromosome, ranging from 19,659,488 bp to 20,465,244 bp. This region contains 3,999 SNPs and Indels.

The analysis results in Table 2 indicated that two SVs SV_20120488 and SV_20099203, of the 11 SVs, have the high explanation ratio exceeding 85% for the variation of shattering resistance phenotype. Both SVs belong to DEL type. Of which SV_20120488 is located in the downstream region of Sindi_0765000 gene. SV_20099203 is located in the upstream promoter region of Sindi_0765000 gene. Genome annotation indicates that Sindi_0765000 gene is a homolog of HEC3 gene.

In summary, it is hypothesized that SV_20099203 which involves in a deletion of 1050 bp, impacts the upstream promoter sequence of the Sindi_0765000 gene and possibly causes the alteration of gene promoter's activity, thus changes the gene function, and consequently changes the phenotype from shattering-to-shattering resistance in sesame. Thus, the Sindi_0765000 gene is determined as the target gene associated with the sesame shattering resistance trait and thus designated as Sihec3.

Example 2

Based on the identification of target gene in Example 1, the gene and upstream promoter sequences of the sesame shattering gene Sihec3 and its allele SiHEC3 were cloned and aligned. A specific process is briefly introduced as follows.

based on the findings from Example 1 and the fine genome map of Yuzhi 11, primer pairs were designed to clone the target gene Sihec3 and allele SiHEC3. Considering the long length of gene and promoter sequence, the full-length gene sequences of Sihec3 and allele SiHEC3 were obtained through a splicing method using different primer pairs. The specific sequences of the primer pairs used in this process are as follows:

```
Primer 1F forward primer:
5'-TGACGGTCCGATTTGTAAGGTG-3',

Primer 1R reverse primer:
5'-GAAATTCGGAGACGGGAGG-3';
``` according to the preliminary analysis, the amplicons in shattering resistance and shattering germplasm accessions with this primer are 1392 bp and 2432 bp, respectively;

```
Primer2F forward primer:
5'-AGCTAAATCCTCCTCTTTCACCA-3',

Primer2R reverse primer:
5'-ACAGCGTACAGGTTTCATT-3';
``` according to the preliminary analysis, the amplicons in shattering resistance and shattering germplasms with this primer are 3410 bp and 3408 bp, respectively.

Subsequently, PCR amplification for the genomic DNA of the shattering resistance germplasm M7 and the shattering germplasm Yuzhi 11 was performed using the high-fidelity enzyme PrimeSTAR Max DNA Polymerase (Takara product). The amplification process with a 20 µL PCR reaction system is set as below:

DNA template, 1 µL; dNTP Mix (10 mM each), 0.4 µL; 2×Phanta Max Buffer, 10 µL; Phanta Max Super-Fidelity DNA Polymerase, 0.4 µL;

EvaGreen, 1 µL; Primer F, 0.4 µL; Primer R, 0.4 µL; ddH2O, 6.4 µL;

a reference PCR amplification reaction program is denaturation at 98° C. for 10 seconds, renaturation at 55° C. for 5 seconds, extension at 72° C. for 3 minutes and 50 seconds, and cycling 30 times; finally, extension at 72° C. for 5 minutes; the amplified product can be directly performed for electrophoresis analysis or stored at 4° C. for further use.

Ultimately, the amplicons were analyzed using electrophoresis. The products were then purified and sequenced (performed by Shanghai Shenggong Biotechnology Co., Ltd.). After sequenced, the sequences of individual amplicons were assembled.

The analysis results revealed that the full-length genomic sequence of the shattering resistance gene Sihec3 is 3406 bp, including two exons and one intron, with the gene sequence present in SEQ ID No. 1. Similarly, the full-length genomic sequence of the allele SiHEC3 associated with the shattering phenotype, is 3441 bp in length and also comprises two exons and one intron.

Alignment analysis results shown in FIG. 4 reveals that the upstream promoter region and the 5 'UTR region of the shattering resistance gene Sihec3 are missing 1049 bp, differing from the corresponding sequence of allele SiHEC3. Correspondingly, the phenotype changes from the typical shattering trait to shattering resistance trait. Additionally, there is a single nucleotide polymorphism (SNP), an A to C base mutation at the 111th position within the coding sequence (CDS) of both the Sihec3 gene and SiHEC3 allele. This mutation results in an amino acid change from glutamine to histidine at the 37th position in the protein sequence. Compared with the sequences in other varieties, this mutation site also presents in other germplasm accessions with shattering trait and does not influence the shattering phenotype.

Example 3

Building on the findings from Example 2, in order to further validate that Sihec3/SiHEC3 regulates the shattering resistance trait, a primer pair for PCR detection was designed, based on sequence differences in the promoter and gene sequences of Sihec3 and allele SiHEC3, in accordance with molecular breeding technology and PCR principles. The primer pair was designated as SSR1 and specifically crafted as follows:

```
SSR1-F sequence:
5'-TACATGGGCACAAAGAAAC-3';

SSR1-R sequence:
5'-CTGGTGAAAGAGGAGGATT-3'.
```

When detecting and determining the phenotype of shattering trait using SSR1 with the primer pair, a specific process is as below:

(1) extracting a genomic DNA from a sesame sample;

(2) taking the genomic DNA extracted in step (1) as a template, performing a PCR amplification using SSR1 and primer pair; during PCR amplification, a 15 µL reference PCR amplification reaction system is as following:

template DNA (50 ng/µL), 1.0 µL; 2×Phanta Max Buffer, 7.5 µL; Phanta Max Super-Fidelity DNA Polymerase. 0.3 µL;

dNTP Mix, 0.3 µL; Forward Primer (10 µM), 0.3 µL; Reverse Primer (10 µM), 0.3 µL; EvaGreen, 0.75 µL;

adding ultrapure water to 15 µL; a reference PCR amplification reaction program is: denaturation at 98° C. for 10 seconds, renaturation at 55° C. for 5 seconds, extension at 72° C. for 120 seconds, and cycling for 30 times; finally, extension at 72° C. for 5 minutes.

(3) Based on the electrophoresis result of PCR product, the sample can be determined to be shattering or a shattering resistant.

It should be noted that the genetic marker site belongs to SV mutation. Therefore, a specific criterion for phenotype determination is that:

when the amplification has a band with a length of 1724 bp, the sample contains SiHEC3 gene with complete promoter sequence and should be homozygous with seed shattering phenotype;

when the amplification has a band with a length of 684 bp, the sample contains Sihec3 gene sequence with the deletion of promoter sequence and should be homozygous with shattering resistance phenotype;

when the amplification simultaneously has two bands with 1724 bp and 684 bp, the sample should be heterozygous with shattering phenotype.

Based on the above method, 96 natural germplasm accessions and 96 hybrid $F_2$ plantlets of "Yuzhi NS610 (shattering resistance)× Anhui Qingyangbai (shattering)" were randomly chosen for phenotypes detection using the PCR-based genetic marker SSR1.

The results, as partially depicted in FIG. 5), demonstrate that the genotype determined through PCR using the specific primer pair is in accordance with the actual phenotype with 100% accuracy. This result suggests that the gene Sihec3 is indeed the target gene regulating the shattering trait in sesame.

In conclusion, the Sihec3 gene has been identified associated with the regulation of sesame shattering resistance trait and could be used for research in the regulation mechanism of seed growth and development in sesame and other crops. The gene marker SSR1 can be applied in shattering phenotype detection and direct breeding new sesame varieties with enhanced shattering resistance trait.

---

What is claimed is:

1. A *Sesamum indicum* plant or plant part comprising a mutation within an endogenous HECATE 3 gene (Sihec3 gene) that confers a sesame seed shattering resistance trait onto the plant or plant part;

wherein the Sihec3 gene comprises the sequence of SEQ ID No. 1.

2. A *Sesamum indicum* plant or plant part comprising a protein encoded by the Sihec3 gene according to claim 1, wherein the protein comprises the sequence of SEQ ID No. 2.

\*  \*  \*  \*  \*

SEQUENCE LISTING

```
Sequence total quantity: 14
SEQ ID NO: 1              moltype = DNA  length = 3406
FEATURE                  Location/Qualifiers
source                   1..3406
                         mol_type = genomic DNA
                         organism = Sesamum indicum L.
SEQUENCE: 1
gcttctgaat tcatcccttc aaagctaaat cctcctcttt caccagctca agggttgtac   60
ttcttctcag agtacatttt gatcatggat ttgagccatc acaggttcac aaacaccact  120
tgggagccat acaacattcc catggatcaa ggccatctgc tccaagatca aacccctttt  180
gatcatcatc cacacgcaca atggccttac tttcctccaa ttcacagcca aaacgagccg  240
tcggattcct cgcccacgca actcctcccg tctccgaatt tcgaccaaat gggctctgca  300
gccttcaaag cgtcagaagc cggagatcat caagacgacg agcccgaaga ggagttggga  360
gccatgaaag agatgatgtt caagatcgca gcaatgcaac ccgtcgacat cgacccggcc  420
accatccgca agcccaggag gcggaacgtc cggatcagcg acgacccgca gagcgtcgcg  480
gcccgccacc gccgtgagag gatcagtgag aagatccgga tcctccagag actggtcccc  540
gggggcacta agatggacac tgcttccatg ctggatgaag ccattcgcta tgttaagttc  600
ttgaagaggc aaatccgcat actccaggcc aaccaccacc agccgccgtg catagggatc  660
gccactccca ccggcgccgc caccgctgaa gaatgggtgg cggtaacaac caaggccacc  720
gccaccgcca ccgcggcagc agggacgtcg tcttcgtact tgtttggagg gaacaacaat  780
aacgatgggg caggtgatga tatatcaatc ccatatgttt taatttaacc ataagtttta  840
tatattggtg attagcattt caccatataa attagtatat ataattaatt ttgatgatca  900
aacgttgtat tatcataagg tttgtattta aaaattcaaa aaaatccatg tgatgataag  960
aaaaaggtta gttaggatat tgttgactaa ggggGcatcg gaataatcac aaaacggtta 1020
gcctgagtta tttattgtgt gtatatatat aatatatgca agaagggctt tggccctcac 1080
aaacttcttt tattggacta tatttTccct gcccgaaata aaacagtgat gtaagaaaac 1140
tttgaatatc atgactatac tctctctaac acacacgtaa acctgcgtgt acgtgtgtgt 1200
gtttgcaggc ttgtggaaga aagtatagca acctgcagag agcatatata tatgtgtgtg 1260
tgtgtgtgtg tgttttatcc ctaaatatta tgtggattga tgatgaattt gctggtgtct 1320
gatggaccac aagaggccaa gaatgattgt gttctttttg cagtagcaga cgccactttc 1380
actgcatata catcatcatc atcatccatc gatcaaaccc tactcttgca agaaacttga 1440
cgagattttc ctcaacaaca ttaaataaca ccacacacgt ttcttcttct ccctgcattc 1500
agacaacaat gttcaacctt atagcacatt gtcctgaaat ctgcatcgta caaatacgac 1560
ttctatgtat acattttcca tgtatatgt gttgcaattg tgtgcataca catactcagg 1620
gatgtggcgt gtaaaaggaa tatatacata tatagataga taatgtcatt gtgtgtaata 1680
aattgttaag tgtgtaggat aattaaatgt attttttctcc tataatttag gataaaaatt 1740
aaatgccaaa tgctaccaaa atataggatt agaatactac cctagcaagt caaaaacaaa 1800
ataacaaaga acctaagtta tgagaccaaa aatatgttta acccttcgta tgtataatta 1860
atgtatatga ccaactaagt cgtgtttatt aaacttggga tcttttcttc tctaaattcc 1920
tttttttttt tttcaaattt tcttctatat attcatgtga gggggaaata acacttttcg 1980
tccattaatt tagagccttt tcgttttttgg ttcctttaat tacagaattc tcactagtgg 2040
ttctgcaact cctaaaaaat agcattttta ctcctataac acacttttga gctgctaaat 2100
tggtatccaa tgcctgcatg catagtatga tgaattgttt gttagatact gagtgggagc 2160
acagctttat atgtctaatt gtatctttac tcagtatttg tgcaataaaa gtaatacgta 2220
aaatcacact tataggtgtt aatttggctt ctaaacttat taatttataa gatcttataa 2280
ctacatatat tttataaaat aatttaatta tatttttagt ctcataattt tgatcattca 2340
gcattttttag ctagtaacta atcatttcgg cggtttctgt tttcgtgtaa ccaggagaga 2400
tttgatcgga ttttttctcgt gtttactaaa tttgtttca ggtgggcgga aagtggtatg 2460
tgctactcag gtgactgttt ataattaggg caaatcatca tattggctaa ttaatgccat 2520
tttgatgcca gaaagaaaaa ttagccaata ggatgattcg ccctagtttt caacagacac 2580
atgagtggca gatacatttt tcgaccatct cgaaagaaat caggcaaaca ggggaaaatt 2640
gatcaaattt gttctgaatt tgttagagaa aatattacat gacaaaatta caatcttaac 2700
aagttagagg attaaatttt caaatgaaca taattacggg agcaaaaata caattaagcc 2760
tataagatat atatgtatat atataagatg tttcttaagc taagttgcta gattttattc 2820
taaaaagaag gctatttaag tatttgaata aaataaaatt acgaaactaa ttataatacg 2880
ttattaataa tgataaattt gtgactaatt ttttaaaaaa aataatatat ttttaaacta 2940
agttgaaaat ttttacttttt ttctgaagaa gcttataatt ataagctcca aatcttagtt 3000
```

```
tccggatcgt ataatctcat tttccacaaa atttaccaaa cactctgcaa catctgaaaa   3060
ttaagttgta tattactttg ccctattaca actaccatta attaacgttt tatgttctga   3120
taattaacat atatatatat atacacacac acacatatgt gtgtgtgttt ttcataatgc   3180
gatttgcagg tgtggaagca ttcaaatagg agtaaacttg aagagcacat gaactgctgt   3240
cgtcggggta ttctcgagtt cttcaatatt gtgggattct gacttgaccc attgagacaa   3300
agtgtgtagt agaaacttca gtgtattggg cttaatgttg taagaacaga agggcccaaa   3360
gccgccggaa aagagaagat tgtgtcagta gaaaattacg atcaag             3406

SEQ ID NO: 2            moltype = AA   length = 244
FEATURE                 Location/Qualifiers
source                  1..244
                        mol_type = protein
                        organism = Sesamum indicum L.
SEQUENCE: 2
MDLSHHRFTN TTWEPYNIPM DQGHLLQDQT PFDHHPHAQW PYFPPIHSQN EPSDSSPTQL   60
LPSPNFDQMG SAAFKASEAG DHQDDEPEEE LGAMKEMMFK IAAMQPVDID PATIRKPRRR   120
NVRISDDPQS VAARHRRERI SEKIRILQRL VPGGTKMDTA SMLDEAIRYV KFLKRQIRIL   180
QANHHQPPCI GIATPTGAAT AEEWVAVTTK ATATATAAAG TSSSYLFGGN NNNDGAGVEA   240
FNME                                                             244

SEQ ID NO: 3            moltype = DNA   length = 3441
FEATURE                 Location/Qualifiers
source                  1..3441
                        mol_type = genomic DNA
                        organism = Sesamum indicum L.
SEQUENCE: 3
aagcccttaa aagctgcaga gaacctaatc aaagattgct tctgaattca tcccttcaaa   60
gctaaatcct cctctttcac cagctcaagg gttgtacttc ttctcagagt acattttgat   120
catggatttg agccatcaca ggttcacaaa caccacttgg gagccataca acattcccat   180
ggatcaaggc catctgctcc aagatcaaac ccctttgat catcatccac aagcacaatg   240
gccttacttt cctccaattc acagccaaaa cgagccgtcg gattcctcgc ccacgcaact   300
cctcccgtct ccgaatttcg accaaatggg ctctgcagcc ttcaaagcgt cagaagccgg   360
agatcatcaa gacgacgagc ccgaagagga gttgggagcc atgaaagaga tgatgttcaa   420
gatcgcagca atgcaacccg tcgacatcga cccggccacc atccgcaagc ccaggaggcg   480
gaacgtccgg atcagcgacg acccgcagag cgtcgcggcc cgccaccgcc gtgagaggat   540
cagtgagaag atccggatcc tccagagact ggtccccggg ggcactaaga tggacactgc   600
ttccatgctg gatgaagcca ttcgctatgt taagttcttg aagaggcaaa tccgcatact   660
ccaggccaac caccaccagc cgccgtgcat agggatcgcc actcccaccg gcgccgccac   720
cgctgaagaa tgggtgcggg taacaaccaa ggccaccgcc accgccaccg cggcagcagg   780
gacgtcgtct tcgtacttgt ttggagggaa caacaataac gatgggggcag gtgatgatat   840
atcaatccca tatgttttaa tttaaccata agttttatat attggtgatt agcatttcac   900
catataaatt agtatataaa ttaattttga tgatcaaacg ttgtattatc ataaggtttg   960
tatttaaaaa ttcaaaaaaa tccatgtgat gataagaaaa aggtttgtta ggatattgtt   1020
gactaagggg gcatcggaat aatcacaaaa cggttagcct gagttattta ttgtgtgtat   1080
atatataata tatgcaagaa gggctttggc cctcataaac ttcttttatt ggcctatatt   1140
ttccctgccc gaaataaaac agtgatgtaa gaaaactttg aatatcatga ctatactctc   1200
tctaacacac acgtaaacct gcgtgtacgt gtgtgtgttt gcaggcttgt ggaagaaagt   1260
atagcaacct gcagagagca tatatatata tatgtgtgtg tgtgtgtgtg ttttatccct   1320
aaatattatg tggattgatg atgaatttgc tggtgtctga tggaccacaa gaggccaaga   1380
atgattgtgt tcttttgcag tagcagacgc cactttcact gcatatacat catcatcatc   1440
catcgatcaa accctactct tgcaagaaac ttggcgaaat tttcctcaac aacattaaat   1500
aacaccacac acgtttcttc ttctccctgc attcagacaa caatgttcaa ccttatagca   1560
cattgtcctg aaatctgcat cgtacaaata cgacttctat gtatacattt tccagtgtat   1620
atgtgttgca attgtgtgca tacacatact cagggatgtg gcgtgtaaaa ggaatatata   1680
catatatata tataatgtca atgtgtgtaa taaattgtta agtgtgtagg ataattaaat   1740
gtatttttttc tcctataatt taggataaaa attaaatacc aaatactacc aaaatatagg   1800
attagaaatac taccctaaaa agtcaaaaca aaaataacaa ataacctaaa ttatgagacc   1860
aaaaatatgt ttaaccctttc atatgtatga cttgtataat taatgtattt taccagctaa   1920
gtcgtgttta ttaaacttgg gatctttttct tctctatatt ccttttttttt tttttcaaat   1980
tttcttctat atattcatgt gagggggaaa taacacttt cgtccagtaa tttagagcct   2040
tttcatttttt ggttcctttta gttacaaaat tctcattagt ggttctgtaa ctcctaaaaa   2100
atagcatttt tactcctata acacactttt gagctgctaa attggtatcc aatgcctgca   2160
tgcatagtat gatgaattgt ttgttagata ctgagtggga gcacagcttt atatgtctaa   2220
ttgtatcttt actcaatatt tgtgcaataa agtaatacg taaaatcaca cttataggtg   2280
ttaatttggc ttctaaactt attaatttat aagatcttat aactacatat ataaaataat   2340
ttaattatat ttttagtctc ataatttttga tcattcagca tttttagcta gtaactaatc   2400
atttcggcgt tttctgtttt cgtgtaacca agagagattt gatcggattt ttctcgtgtt   2460
tactaaattt gtttttcaggt gggcgaaaag tggtatgtgc tactcaggtg actgtttata   2520
attagggcaa atcatcatat tggctaatta atgccatttt gatgccagaa agaaaattag   2580
ccaataggat gattcgtcct agttttcaac agacacatga gtggcagata catttttcga   2640
ccatctcgaa agaaatcagg caaacaggaa aaaattgatc aaatttgttc tgaatttgtt   2700
agagaaaaaa ttacatgatc aaaattacaat cttaacaagt tagaggatta aattttcaaa   2760
tggacaaaat tacgggagta aaaatacaat taagcctata agatatatat gtatatatat   2820
aagatgtttc ttaagctaag ttgctagatt ttattctaaa aagaaggcta tttaagtatt   2880
tgaataaaat aaaattacga aactaattat aatacgttat taataatgat aaatttgtga   2940
ctaatttttaa aaaaaattaa tatattttta aactaagttg aaaattttta ctttttttctg   3000
aagaagctta taattataag ctccaaatct tagtttccgg atcgtataat ctcatttttcc   3060
acaaaattta ccaaacactc tgcaacatct gaaaattaag ttgtatatta ctttgcccta   3120
ttacaactac cattaattaa cgttttatgt tctgataatt aacatatata tatatacaca   3180
```

```
cacacacaca tatgtatgtg tgtttttcat aatgcgattt gcaggtgtgg aagcattcaa   3240
tatggagtaa acttgaagag cacatgaact gctgtcgtcg gggtattctc gagttcttca   3300
atattgtggg attctgactt gacccattga gacaaagtgt gtggtagaaa cttcagtgta   3360
ttgggcttaa tgttgtaaga acagaagggc ccaaagccgc cggaaaagag aagattgtgt   3420
cagtagaaaa ttacgatcaa g                                             3441

SEQ ID NO: 4              moltype = AA   length = 244
FEATURE                   Location/Qualifiers
source                    1..244
                          mol_type = protein
                          organism = Sesamum indicum L.
SEQUENCE: 4
MDLSHHRFTN TTWEPYNIPM DQGHLLQDQT PFDHHPQAQW PYFPPIHSQN EPSDSSPTQL   60
LPSPNFDQMG SAAFKASEAG DHQDDEPEEE LGAMKEMMFK IAAMQPVDID PATIRKPRRR   120
NVRISDDPQS VAARHRRERI SEKIRILQRL VPGGTKMDTA SMLDEAIRYV KFLKRQIRIL   180
QANHHQPPCI GIATPTGAAT AEEWVAVTTK ATATATAAAG TSSSYLFGGN NNNDGAGVEA   240
FNME                                                               244

SEQ ID NO: 5              moltype = DNA   length = 735
FEATURE                   Location/Qualifiers
source                    1..735
                          mol_type = other DNA
                          organism = Sesamum indicum L.
SEQUENCE: 5
atggatttga gccatcacag gttcacaaac accacttggg agccatacaa cattcccatg   60
gatcaaggcc atctgctcca agatcaaacc ccttttgatc atcatccaca cgcacaatgg   120
ccttactttc ctccaattca cagccaaaac gagccgtcgg attcctcgcc cacgcaactc   180
ctcccgtctc cgaatttcga ccaaatgggc tctgcagcct tcaaagcgtc agaagccgga   240
gatcatcaag acgacgagcc cgaagaggag ttgggagcca tgaaagagat gatgttcaag   300
atcgcagcaa tgcaacccgt cgacatcgac ccggccacca tccgcaagcc caggaggcgg   360
aacgtccgga tcagcgacga cccgcagagc gtcgcggccc gccaccgccg tgagaggatc   420
agtgagaaga tccggatcct ccagagactg gtccccgggg gcactaagat ggacactgct   480
tccatgctgg atgaagccat tcgctatgtt aagttcttga gaggcaaat ccgcatactc   540
caggccaacc accaccagcc gccgtgcata gggatcgcca ctcccaccgg cgccgccacc   600
gctgaagaat gggtggcggt aacaaccaag gccaccgcca ccgccaccgc ggcagcaggg   660
acgtcgtctt cgtacttgtt tggagggaac aacaataacg atggggcagg tgtggaagca   720
ttcaatatgg agtaa                                                   735

SEQ ID NO: 6              moltype = DNA   length = 735
FEATURE                   Location/Qualifiers
source                    1..735
                          mol_type = other DNA
                          organism = Sesamum indicum L.
SEQUENCE: 6
atggatttga gccatcacag gttcacaaac accacttggg agccatacaa cattcccatg   60
gatcaaggcc atctgctcca agatcaaacc ccttttgatc atcatccaca gcacaatgg   120
ccttactttc ctccaattca cagccaaaac gagccgtcgg attcctcgcc cacgcaactc   180
ctcccgtctc cgaatttcga ccaaatgggc tctgcagcct tcaaagcgtc agaagccgga   240
gatcatcaag acgacgagcc cgaagaggag ttgggagcca tgaaagagat gatgttcaag   300
atcgcagcaa tgcaacccgt cgacatcgac ccggccacca tccgcaagcc caggaggcgg   360
aacgtccgga tcagcgacga cccgcagagc gtcgcggccc gccaccgccg tgagaggatc   420
agtgagaaga tccggatcct ccagagactg gtccccgggg gcactaagat ggacactgct   480
tccatgctgg atgaagccat tcgctatgtt aagttcttga gaggcaaat ccgcatactc   540
caggccaacc accaccagcc gccgtgcata gggatcgcca ctcccaccgg cgccgccacc   600
gctgaagaat gggtggcggt aacaaccaag gccaccgcca ccgccaccgc ggcagcaggg   660
acgtcgtctt cgtacttgtt tggagggaac aacaataacg atggggcagg tgtggaagca   720
ttcaatatgg agtaa                                                   735

SEQ ID NO: 7              moltype = DNA   length = 22
FEATURE                   Location/Qualifiers
source                    1..22
                          mol_type = other DNA
                          organism = Sesamum indicum L.
SEQUENCE: 7
tgacggtccg atttgtaagg tg                                            22

SEQ ID NO: 8              moltype = DNA   length = 19
FEATURE                   Location/Qualifiers
source                    1..19
                          mol_type = other DNA
                          organism = Sesamum indicum L.
SEQUENCE: 8
gaaattcgga gacgggagg                                                19

SEQ ID NO: 9              moltype = DNA   length = 23
FEATURE                   Location/Qualifiers
source                    1..23
                          mol_type = other DNA
                          organism = Sesamum indicum L.
```

```
SEQUENCE: 9
agctaaatcc tcctctttca cca                                                          23

SEQ ID NO: 10              moltype = DNA   length = 19
FEATURE                    Location/Qualifiers
source                     1..19
                           mol_type = other DNA
                           organism = Sesamum indicum L.
SEQUENCE: 10
acagcgtaca ggtttcatt                                                               19

SEQ ID NO: 11              moltype = DNA   length = 19
FEATURE                    Location/Qualifiers
source                     1..19
                           mol_type = other DNA
                           organism = Sesamum indicum L.
SEQUENCE: 11
tacatgggca caaagaaac                                                               19

SEQ ID NO: 12              moltype = DNA   length = 19
FEATURE                    Location/Qualifiers
source                     1..19
                           mol_type = other DNA
                           organism = Sesamum indicum L.
SEQUENCE: 12
ctggtgaaag aggaggatt                                                               19

SEQ ID NO: 13              moltype = DNA   length = 4543
FEATURE                    Location/Qualifiers
source                     1..4543
                           mol_type = other DNA
                           organism = Sesamum indicum L.
SEQUENCE: 13
tgacggtccg atttgtaagg tgatagggat gatcgaaaga ttgtttcccc aaccttggat     60
gcattagacg ttgctgctgg aagtggcgtg ctacgaccat attaacgtga tacaggaggc     120
gtaccactag acataattaa tacaaattat agtaaacatt agtttttata attgctgaaa     180
aaattaacct aattcaataa tttatgttga atttatgatt attgtactca ttaattactt     240
aaaaatatat agttcctttg tacacatata caaacgggtc aagcattgct tttaacttct     300
ttagcatatc acataaattt ttttgttata gtactactcc agtttgtcca ctctttttct     360
gtcaacattg tcttctcttt acaaataaga atggataaac ctgactaatt cattctacta     420
agaaaaaatc acttgatgag ctaaaaaagc taaagcaatg cttgatccat ttgtacatgg     480
gcacaaagaa actatacatt tttaatgact cttattgaaa atattattat tggaactatt     540
agcctaatat tgtgattatt gacataatta tgtaaatagt gttatgtgaa tactagtctt     600
gtgattgtta atattattat gtaaataatg ttattattgt gaatattagt ctaattttgc     660
gattgttgac attattatgt aaataatgtt attatttaga atattgaata acgttgtgat     720
tattgatatt attatgtaaa taatattatt cttgaaaata ttagcctaaa ttttgtgatt     780
attgacatta ttttgtaaat aatattatta ttgagaatat tgatctaatt ttatgattat     840
tgacattatt aaataaataa tattatcatt tgaaatatta gcttaaaggt tgtgaatact     900
gacattgtta tgtaaataat gttattattg aaaattgtaa tcgaattttg tgattgttga     960
cattattatg taaataataa tattaatgaa aaaatgcaag aattacatca attacaccac     1020
tatgtaaatt acacaaatatg atacaataca cacaaaaatt ggggtcacga tgtcatatac     1080
caaatttcat tcctaatgtg ttccaatact cgcttctgaa ttcatccctt caaagctaaa     1140
tcctcctctt tcaccagctc aagggttgta cttcttctca gagtacattt tgatcatgga     1200
tttgagccat cacaggttca caaacaccac ttgggagcca tacaacattc ccatggatca     1260
aggccatctg ctccaagatc aaaccccttt tgatcatcat ccacacgcac aatggcctta     1320
ctttcctcca attcacagcc aaaacgagcc gtcggattcc tcgcccacgc aactcctccc     1380
gtctccgaat ttcgaccaaa tgggctctgc agccttcaaa gcgtcagaag ccggagatca     1440
tcaagacgac gagcccgaag aggagttggg agccatgaaa gagatgatgt tcaagatcgc     1500
agcaatgcaa cccgtcgaca tcgacccggc caccatccgc accaacagga ggcggaacgt     1560
ccggatcagc gacgacccgc agagcgtcgc ggcccgccac cgccgtgaga ggatcagtga     1620
gaagatccgg atcctccaga gactggtccc cggggggcact aagatggaca ctgcttccat     1680
gctggatgaa gccattcgct atgttaagtt cttgaagagg caaatccgca tactccaggc     1740
caaccaccac cagccgccgt gcatagggat cgccactccc accggcgccg ccaccgctga     1800
agaatggggtg gcggtaacaa ccaaggccac cgccaccgcc accgccggga cagggacgtc     1860
gtcttcgtac ttgtttggag ggaacaacaa taacgatggg gcaggtgatg atatatcaat     1920
cccatatgtt ttaatttaac cataagtttt atatattggt gattagcatt tcaccatata     1980
aattagtata tataattaat tttgatgatc aaacgttgta ttatcataag gtttgtattt     2040
aaaaattcaa aaaaatccat gtgatgataa gaaaaaggtt tgttaggata ttgttgacta     2100
aggggggcatc ggaataatca caaaacggtt agcctgagtt atttattgtg tgtatatata     2160
taatatatgc aagaagggct ttggccctca caaacttctt ttattggact atattttccc     2220
tgcccgaaat aaaacagtga tgtaagaaaa cttttgaatat catgactata ctctctctaa     2280
cacacacgta aacctgcgtg tacgtgtgtg tgtttgcagg cttgtggaag aaagtatagc     2340
aacctgcaga gagcatatat atatgtgtgt gtgtgtgtgt gtgtttttatc cctaaatatt     2400
atgtgttgga tgatgaatt tgctggtgtc tgatgaacca caagaggcca agaatgattg     2460
tgttcttttt gcagtagcag acgccacttt cactgcatat acatcatcat catcatccat     2520
cgatcaaacc ctactcttgc aagaaacttg acgagatttt cctcaacaac attaaataac     2580
accacacacg tttcttcttc tccctgcatt cagacaacaa tgttcaacct tatagcacat     2640
tgtcctgaaa tctgcatcgt acaaatacga cttctatgta tacattttcc agtgtatatg     2700
tgttgcaatt gtgtgcatac acatactcag ggatgtggcg tgtaaaagga atatatacat     2760
```

```
atatagatag ataatgtcat tgtgtgtaat aaattgttaa gtgtgtagga taattaaatg  2820
tatttttctc ctataattta ggataaaaat taaatgccaa atgctaccaa aatatataggat  2880
tagaatacta ccctagcaag tcaaaaacaa aataacaaag aacctaagtt atgagaccaa  2940
aaaatatgttt aacccttcgt atgtataatt aatgtatatg accaactaag tcgtgtttat  3000
taaacttggg atctttttctt ctctaaattc ctttttttttt ttttcaaatt ttcttctata  3060
tattcatgtg aggggggaaat aacacttttc gtccattaat ttagagcctt ttcgttttttg  3120
gttcctttaa ttacagaatt ctcactagtg gttctgcaac tcctaaaaaa tagcattttt  3180
actcctataa cacactttttg agctgctaaa ttggtatcca atgcctgcat gcatagtatg  3240
atgaattgtt tgttagatac tgagtgggag cacagctttta tatgtctaat tgtatctttta  3300
ctcagtattt gtgcaataaa agtaatacgt aaaatcacac ttataggtgt taatttggct  3360
tctaaactta ttaatttata agatcttata actacatata ttttataaaa taatttaatt  3420
atatttttag tctcataatt ttgatcattc agcattttta gctagtaact aatcatttcg  3480
gcggtttctg ttttcgtgta accaggagag atttgatcgg attttttctcg tgtttactaa  3540
atttgtttttc aggtgggcgg aaagtggtat gtgctactca ggtgactgtt tataattagg  3600
gcaaatcatc atattggcta attaatgcca ttttgatgcc agaaagaaaa attagccaat  3660
aggatgattc gccctagttt tcaacagaca catgagtggc agatacattt ttcgaccatc  3720
tcgaaagaaa tcaggcaaac aggggaaaat tgatcaaatt tgttctgaat ttgttagaga  3780
aaatattaca tgacaaaatt acaatcttaa caagttagag cgttaaattt tcaaatgaac  3840
ataattacgg gagcaaaaat acaattaagc ctataagata tatatgtata tatataagat  3900
gtttcttaag ctaagttgct agatttttatt ctaaaaagaa ggctatttaa gtatttgaat  3960
aaaataaaat tacgaaacta attataatac gttattaata atgataaatt tgtgactaat  4020
tttttaaaaa aaataatata ttttttaaact aagttgaaaa tttttacttt tttctgaaga  4080
agcttataat tataagctcc aaatcttagt ttccggatcg tataatctca ttttccacaa  4140
aatttaccaa acactctgca acatctgaaa attaagttgt atattacttt gccctattac  4200
aactaccatt aattaacgtt ttatgttctg ataattaaca tatatatata tatacacaca  4260
cacacatatg tgtgtgtgtt tttcataatg cgatttgcag gtgtggaagc attcaatatg  4320
gagtaaactt gaagagcaca tgaactgctg tcgtcggggt attctcgagt tcttcaatat  4380
tgtgggattc tgacttgacc cattgagaca aagtgtgtag tagaaacttc agtgtattgg  4440
gcttaatgtt gtaagaacag aagggcccaa agccgccgga aaagagaaga ttgtgtcagt  4500
agaaaattac gatcaagtgt gtgaaatgaa acctgtacgc tgt                      4543
```

```
SEQ ID NO: 14          moltype = DNA  length = 5581
FEATURE                Location/Qualifiers
source                 1..5581
                       mol_type = other DNA
                       organism = Sesamum indicum L.
SEQUENCE: 14
tgacggtccg atttgtaagg tgatagggat gattgaaaga ttgtttcccc aaccttggat  60
gcattagacg gtgctgctgg aagtgcgtg ctacgaccat agtaacgtga tacaggaggc  120
gcaccactag acataattaa tacaaattat aataaacatt agtttttata attgccgaaa  180
aaattaacct aattcaataa tttatgttga atttatgatt attgtactca ttaattactt  240
aaaaatatat agttcctttg tacagatata caaacgggtc aagcattgct tttaacttct  300
ttagcatatc acataaattt ttttgttata ctactactcc agtttgtcca ctcttttttct  360
gtcaacattg tcttctcttt acaaataaga atggataaac ttgactaatt aattctactg  420
agaaaaaatc acttgatgag ctaaaaaagc taaagcaatg cttgatccat ttgtacatgg  480
gcacaaagaa actatacatt tttaataact cttattgaaa atattattat tggaactatc  540
agcctaatat tgtgattatt gacataatta tgtaaaatagt attatgtgaa tactagtctt  600
gtgattgtta atattattat gtaaataatg ttattattgt gaatattagt ctaactttgc  660
gattgttgac attattatgt aaataatatt attatttaga atattgaata atgttgtgat  720
tattgatatt attatgtaaa taatattatt cttgaaaata ttagcctaaa ttttgtgatt  780
atgacattat tttgtaaata atattattat cgggaatatt gatctaattt tatgattatt  840
gacattatta aataaataat attatcattt gaaatattag cttaaaggtt gtgaatactg  900
acattgttat gtaaataatg ttattattga aaattgtaat cgaattttat gattgttgac  960
attattatgt aaataataat attaatgaaa aaatacatga attacaccac tatgtaaatt  1020
acacaatatg atacaataca cacaaaaatt gggggtcatg atgtcatata ccaaatttca  1080
ttcctaatgt gttccaatac tcgtttcaat gtgaaacggt cgagttatcc gtgtcaaatt  1140
ctattttttc tttttttgta gtgtatgact attacagctc tgagcatgtc tcaaataata  1200
attatctttg tttttgaaca aaaatattaa ttatctttaa tgcatagaga aatggctatt  1260
tttaagctgt aaagaagcaa ttatatgaga gtgagagctc ttagtttaga caattattga  1320
taactcatca gcaagtgcat ttgattgtga ggtcattatc accattaata aaagtgatca  1380
taacatcaat atcatcagta atcatgttta tgatcaatta atcagaataa ttcaattcgt  1440
ctttgctgtg taatttgatt ttttacaata aaacttaatt gcattttttag ttcaaaaatt  1500
atatacaatt atttgacact ttagtcctgt aatttatttg agttataaaa gtagtctcat  1560
tttttttaat tctgcaattt taagacaaaa ttggtcaaat attcaaagtt gacctgaatt  1620
ctgatgccac ttttttcagcta atttttaaaaa tttcaatcag atttgccata aacttgcaaa  1680
attaaaataa ggtgaagaac taatttacaa cctaattaac aagttaccaa actaatataa  1740
aaatgactat aattttgttt aaatctaata attatgaaat gaataatagc ttttctcatt  1800
gaatatttta ttcataatat atgattcttt ttttgtgttc aataaagaat atggggaacc  1860
gtacttggga tggaaagcct tgtttgaaaa cagcaaaccc tagaaagggt tctaacaatc  1920
tgcaatgaaa aaattcacag ccctttactt catcattttca tagtatatca aaaggggtgg  1980
tcccatcaac attaatcaat ctccctacgt tgtttctttc tctttaaatt ccctcaaatt  2040
tcctctctct ctctctctct ctctctctct atatatatat atatatatat atatacacac  2100
acttaaatgc atcaaagccc ttaaaagctg cagagaacct aatcaaagat tgcttctgaa  2160
ttcatccctt caaagctaaa tctcctctctt tcaccagctca aagggttgta cttcttctca  2220
gagtacattt tgatcatgga tttgagccat cacaggttca caaacaccac ttgggagcca  2280
tacaacattc ccatggatca aggccatctg ctccaagatc aaaccccttt tgatcatcat  2340
ccacaagcac aatggcctta ctttcctcca attcacagcc aaaacgagcc gtcggattcc  2400
tcgcccacgc aactcctccc gtctccgaat ttcgaccaaa tgggctctgc agccttcaaa  2460
gcgtcagaag ccggagatca tcaagacgac gagcccgaag aggagttggg agccatgaaa  2520
```

-continued

```
gagatgatgt tcaagatcgc agcaatgcaa cccgtcgaca tcgacccggc caccatccgc   2580
aagcccagga ggcggaacgt ccggatcagc gacgacccgc agagcgtcgc ggcccgccac   2640
cgccgtgaga ggatcagtga gaagatccgg atcctccaga gactggtccc cgggggcact   2700
aagatggaca ctgcttccat gctggatgaa gccattcgct atgttaagtt cttgaagagg   2760
caaatccgca tactccaggc caaccaccac cagccgccgt gcatagggat cgccactccc   2820
accggcgccg ccaccgctga agaatgggtg gcggtaacaa ccaaggccac cgccaccgcc   2880
accgcggcag cagggacgtc gtcttcgtac ttgtttggag ggaacaacaa taacgatggg   2940
gcaggtgatg atatatcaat cccatatgtt ttaatttaac cataagtttt atatattggt   3000
gattagcatt tcaccatata aattagtata taaattaatt ttgatgatca aacgttgtat   3060
tatcataagg tttgtattta aaaattcaaa aaaatccatg tgatgataag aaaaaggttt   3120
gttaggatat tgttgactaa gggggcatcg gaataatcac aaaacggtta gcctgagtta   3180
tttattgtgt gtatatatat aatatatgca agaagggctt tggccctcat aaacttcttt   3240
tattggccta tattttccct gcccgaaata aaacagtgat gtaagaaaac tttgaatatc   3300
atgactatac tctctctaac acacacgtaa acctgcgtgt acgtgtgtgt gtttgcaggc   3360
ttgtggaaga aagtatagca acctgcagag agcatatata tatatatgtg tgtgtgtgtg   3420
tgtgtttat ccctaaatat tatgtggatt gatgatgaat ttgctggtgt ctgatggacc   3480
acaagaggcc aagaatgatt gtgttctttt gcagtagcag acgccacttt cactgcatat   3540
acatcatcat catccatcga tcaaacccta ctcttgcaag aaacttggcg agattttcct   3600
caacaacatt aaataacacc acacacgttt cttcttctcc ctgcattcag acaacaatgt   3660
tcaaccttat agcacattgt cctgaaatct gcatcgtaca aatacgactt ctatgtatac   3720
attttccagt gtatatgtgt tgcaattgtg tgcatacaca tactcaggga tgtggcgtgt   3780
aaaaggaata tatacatata tatatataat gtcaatgtgt gtaataaatt gttaagtgtg   3840
taggataatt aaatgtattt tttctcctat aatttaggat aaaaattaaa taccaaatac   3900
taccaaaata taggattaga atactaccct aaaaagtcaa aacaaatata acaaataacc   3960
taaattatga gaccaaaaat atgtttaacc cttcatatgt atgacttgta taattaatgt   4020
attttaccag ctaagtcgtg tttattaaac ttgggatctt ttcttctcta tattcctttt   4080
ttttttttc aaattttctt ctatatattc atgtgagggg gaaataacac ttttcgtcca   4140
gtaatttaga gccttttcat ttttggttcc tttagttaca aaattctcat tagtggttct   4200
gtaactccta aaaaatagca tttttactcc tataacacac ttttgagctg ctaaattggt   4260
atccaatgcc tgcatgcata gtatgatgaa ttgtttgtta gatactgagt gggagcacag   4320
ctttatatgt ctaattgtat ctttactcaa tatttgtgca ataaaagtaa tacgtaaaat   4380
cacacttata ggtgttaatt tggcttctaa acttattaat ttataagatc ttataactac   4440
atatataaaa taatttaatt atatttttag tctcataatt ttgatcattc agcattttta   4500
gctagtaact aatcatttcg gcgttttctg ttttcgtgta accaagagag atttgatcgg   4560
atttttctcg tgtttactaa atttgttttc aggtgggcga aaagtggtat gtgctactca   4620
ggtgactgtt tataattagg gcaaatcatc atattggcta attaatgcca ttttgatgcc   4680
agaaagaaaa ttagccaata ggatgattcg tcctagtttt caacagacac atgagtggca   4740
gatacatttt tcgaccatct cgaaagaaat caggcaaaca ggaaaaaatt gatcaaattt   4800
gttctgaatt tgttagagaa aaaattacat gatcaaatta caatcttaac aagttagagg   4860
attaaatttt caaatggaca aaaattacggg agtaaaaata caattaagcc tataagatat   4920
atatgtatat atataagatg tttcttaagc taagttgcta gattttattc taaaaagaag   4980
gctatttaag tatttgaata aaataaaatt acgaaactaa ttataatacg ttattaataa   5040
tgataaattt gtgactaatt ttaaaaaaaa ttaatatatt tttaaactaa gttgaaaatt   5100
tttacttttt tctgaagaag cttataatta taagctccaa atcttagttt ccggatcgta   5160
taatctcatt ttccacaaaa tttaccaaac actctgcaac atctgaaaat taagttgtat   5220
attactttgc cctattacaa ctaccattaa ttaacgtttt atgttctgat aattaacata   5280
tatatatata cacacacaca cacatatgta tgtgtgtttt tcataatgcg atttgcaggt   5340
gtggaagcat tcaatatgga gtaaacttga agagcacatg aactgctgtc gtcggggtat   5400
tctcgagttc ttcaatattg tgggattctg acttgaccca ttgagacaaa gtgtgtggta   5460
gaaacttcag tgtattgggc ttaatgttgt aagaacagaa gggcccaaag ccgccggaaa   5520
agagaagatt gtgtcagtag aaaattacga tcaagtgtgt gaaatgaaac ctgtacgctg   5580
t                                                                    5581
```